US008486887B2

(12) United States Patent
Adang et al.

(10) Patent No.: US 8,486,887 B2
(45) Date of Patent: Jul. 16, 2013

(54) ENHANCEMENT OF *BACILLUS THURINGIENSIS* CRY PROTEIN TOXICITIES TO COLEOPTERANS, AND NOVEL INSECT CADHERIN FRAGMENTS

(75) Inventors: Michael J. Adang, Athens, GA (US); Mohd Amir Fursan Abdullah, Watkinsville, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 154 days.

(21) Appl. No.: 12/672,974

(22) PCT Filed: Aug. 11, 2008

(86) PCT No.: PCT/US2008/072806
§ 371 (c)(1),
(2), (4) Date: Apr. 15, 2011

(87) PCT Pub. No.: WO2009/023636
PCT Pub. Date: Feb. 19, 2009

(65) Prior Publication Data

US 2011/0183896 A1 Jul. 28, 2011

Related U.S. Application Data

(60) Provisional application No. 60/964,249, filed on Aug. 10, 2007, provisional application No. 61/084,952, filed on Jul. 30, 2008.

(51) Int. Cl.
*A61K 38/00* (2006.01)
*C07K 14/00* (2006.01)

(52) U.S. Cl.
USPC .......... 514/4.5; 514/1.1

(58) Field of Classification Search
USPC .......... 514/4.5
See application file for complete search history.

(56) References Cited

U.S. PATENT DOCUMENTS

| | | | | |
|---|---|---|---|---|
| 5,106,620 | A | 4/1992 | Hickle et al. | |
| 2004/0127695 | A1 | 7/2004 | Rupar et al. | |
| 2005/0283857 | A1 * | 12/2005 | Adang et al. | 800/302 |
| 2006/0218666 | A1 * | 9/2006 | Isaac et al. | 800/279 |
| 2006/0288448 | A1 * | 12/2006 | Abad et al. | 800/279 |

OTHER PUBLICATIONS

Siegfried, et al., Expressed sequence tags from *Diabrotica virgifera virgifera* midgut identity a coleopteran cadherin and a diversity of cathepsins, Insect Molecular Biology 2005, p. 137-143.
Sayed, et al., A novel cadherin-like gene from western corn rootworm, *Diabrotica virgifera virgifera* (Coleoptera : Chrysomelidae), larval midgut tissue, Oct. 2007, Insect Molecular Biology, vol. 16, NR. 5, XP002593307.
UniProt entry Q5MK05, Uniprot (online), Jul. 22, 200S [retrieved on Dec. 4, 2009) Retrieved from the internet, URL:http://www.uniprot.org/uniprot/Q5MK05.txt?version=20>.

* cited by examiner

*Primary Examiner* — Karlheinz R Skowronek
*Assistant Examiner* — Catherine Mader
(74) *Attorney, Agent, or Firm* — Faegre Baker Daniels LLP

(57) ABSTRACT

The subject invention relates in part to the discovery that a fragment from a cadherin of the western corn rootworm enhances Cry3 toxicity to larvae of naturally susceptible species. The subject invention also relates in part to the discovery that a cadherin fragment from a beetle enhances Cry3Aa and Cry3Bb toxicity to coleopteran larvae, particularly those in the family Chrysomelidae. Such cadherin fragments are referred to as Bt Boosters (BtBs). The subject invention can be extended to the use of BtBs with other coleopteran-toxic Cry proteins for controlling a wide range of coleopterans.

6 Claims, 7 Drawing Sheets

Abbreviations: SIG – signal peptide
CR – cadherin repeat
MPED – membrane proximal extracellular domain
TM – transmembrane domain
CD – cytoplasmic domain
PS – Protease stable

*Significant enhancement was observed for (A) Ms-CR10-12(PS), (B) Ms-CR10-12, and (C) Tm-CR10-MPED. The mass of Cry3Aa was based on gel determination (equivalent to 12.5 ug/ml Bt *tenebrionis* powder).

CR8-10 = Dv-CR8-10

CR8-10 = Dv-CR8-10

*Significant enhancement was observed. Dv-CR8-10(PS) was a better overall enhancer compared to Ms-CR10-12(PS) and Dv-CR8-10.

ENHANCEMENT OF *BACILLUS THURINGIENSIS* CRY PROTEIN TOXICITIES TO COLEOPTERANS, AND NOVEL INSECT CADHERIN FRAGMENTS

This application is a National Stage filing of PCT International Application Serial No. PCT/US2008/72806, filed 11 Aug. 2008, which claims the benefit of U.S. Provisional Application Ser. Nos. 60/964,249, filed 10 Aug. 2007, and 61/084,952 filed 30 Jul. 2008, the disclosures each of which are expressly incorporated herein by reference.

This invention was made in part with government support under USDA award no. 2004-35607-14936. The government has certain rights in this invention.

BACKGROUND OF THE INVENTION

The Cry3 class of *Bacillus thuringiensis* (Bt) Cry proteins is known for toxicity to coleopteran larvae in the family Chrysomelidae. The Cry3Aa and Cry3Bb insecticidal proteins of *Bacillus thuringiensis* (Bt) are used in biopesticides and transgenic crops to control larvae of leaf feeding beetles and rootworms. Due to limited efficacy of Cry3-based biopesticides and the success of competing chemical pesticides, these biopesticides have had limited usage and sales (Gelernter, 2004). Cry3Bb is toxic to corn rootworms (Donovan et al., 1992; Johnson et al., 1993), and a modified version is expressed in commercialized MON863 corn hybrids (Vaughn et al., 2005).

Cry3 toxins have a mode-of-action that is similar yet distinct from the action of lepidopteran-active Cry1 toxins. The Cry3A protoxin (73-kDa) lacks the large C-terminal region of the 130-kDa Cry1 protoxins, which is removed by proteases during activation to toxin. Cry3A protoxin is activated to a 55-kDa toxin and then further cleaved within the toxin molecule (Carroll et al., 1997; Loseva et al., 2002). Activated Cry3A toxin binds to brush border membrane vesicles (BBMV) with a Kd ~37 nM (Martinez-Ramirez and Real, 1996) and recognizes a 144-kDa binding protein in BBMV prepared from the yellow mealworm *Tenebrio molitor* (Coleoptera: Tenebrionidae) (Belfiore et al., 1994). Ochoa-Campuzano et al. (Ochoa-Campuzano et al., 2007) identified an ADAM metalloprotease as a receptor for Cry3Aa toxin in CPB larvae.

Structural differences between Cry3Bb and Cry3Aa toxins could account for the unique rootworm activities of Cry3Bb toxin. As noted by Galitsky et al. (Galitsky et al., 2001), differences in toxin solubility, oligomerization, and binding are reported for these Cry3 toxins. Recently, Cry3Aa was modified to have activity against western corn rootworm (WCRW) *Diabrotica virgifera virgifera* (Coleoptera: Chrysomelidae (Walters et al., 2008). Those authors introduced a chymotrypsin/cathepsin G into domain 1 of Cry3Aa that allowed processing of the 65-kDa form to a 55-kDa toxin that bound rootworm midgut.

Cadherins localized in the midgut epithelium function as receptors for Cry toxins in lepidopteran and dipteran larvae. Sayed et al. (2007) identified a novel cadherin-like gene in WCRW and proposed this protein as a candidate Bt toxin receptor. The cadherin-like gene is highly expressed in midgut tissue of larval stages. The encoded protein is conserved in structure relative to other insect midgut cadherins.

An important Cry1 toxin binding site is localized within the final cadherin repeat (CR) 12 of cadherins from tobacco hornworm *Manduca sexta* (Lepidoptera: Sphingidae) and tobacco budworm *Heliothis virescens* (Lepidoptera: Noctiudae) (Hua et al., 2004; Xie et al., 2005). Unexpectedly, a fragment of Bt-$R_1$ cadherin, the Cry1A receptor from *M. sexta*, not only bound toxin but enhanced Cry1A toxicity against lepidopteran larvae (Chen et al., 2007). If the binding residues within cadherin repeat 12 (CR) were removed, the resulting peptide lost the ability to bind toxin and lost its function as a toxin synergist. A fragment of a cadherin from *Anopheles gambiae* enhanced the toxicity of the mosquitocidal toxin Cry4Ba to mosquito larvae (Hua et al., 2008).

Terminal cadherin repeats from the Cry1A-binding *M. sexta* cadherin and the Cry4Ba-binding *A. gambiae* cadherin were reported to bind toxin and enhance Cry1A toxicity against lepidopteran larvae and Cry4 toxicity against dipteran larvae (Chen et al., 2007; Hua et al., 2008).

BRIEF SUMMARY OF THE INVENTION

The subject invention relates in part to the discovery that a fragment from a cadherin of the western corn rootworm enhances Cry3 toxicity to larvae of naturally susceptible species. The subject invention also relates in part to the discovery that a cadherin fragment from a beetle enhances Cry3Aa and Cry3Bb toxicity to coleopteran larvae, particularly those in the family Chrysomelidae. Such cadherin fragments are referred to herein as Bt Boosters (BtBs).

The subject invention also relates to the extension of these discoveries to the use of BtBs with other coleopteran-toxic Cry proteins for controlling a wide range of coleopterans.

wild-type BtR1 cadherin of *M. sexta*, the cadherin fragment Ms-CR10-12 (BtB4), and the proteinase-stabilized MsCR10-12(PS) fragment (also called BtB5);

cadherin fragment Tm-CR10-MPED from *Tenebrio molitor* (Coleoptera: Tenebrionidae); and cadherin fragments Dv-CR8-10 from *Diabrotica virgifera virgifera* (Western corn rootworm, WCRW) and the protease stabilized version Dv-CR8-10(PS).

Figure 1:
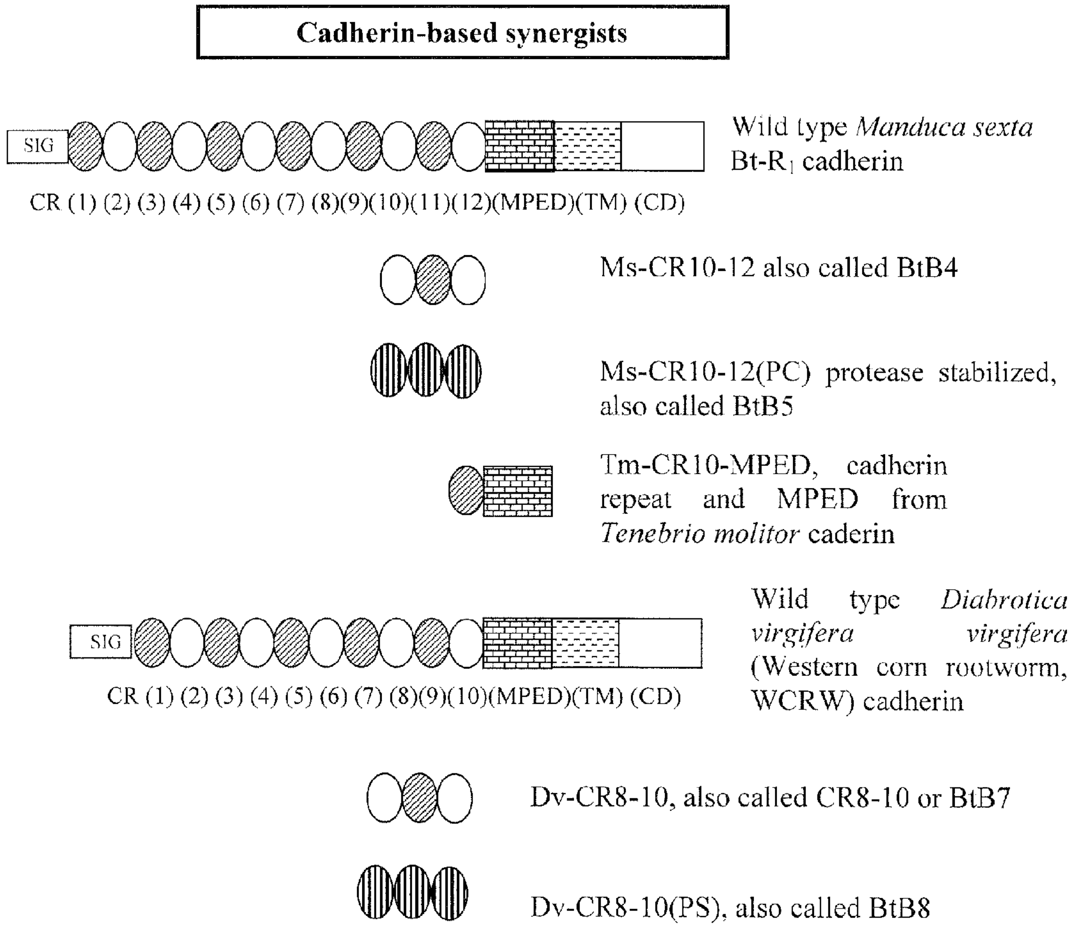
FIG. 1 illustrates wild-type insect cadherin and cadherin fragments (i.e. peptides) with synergistic activities, including.
Figure 2:
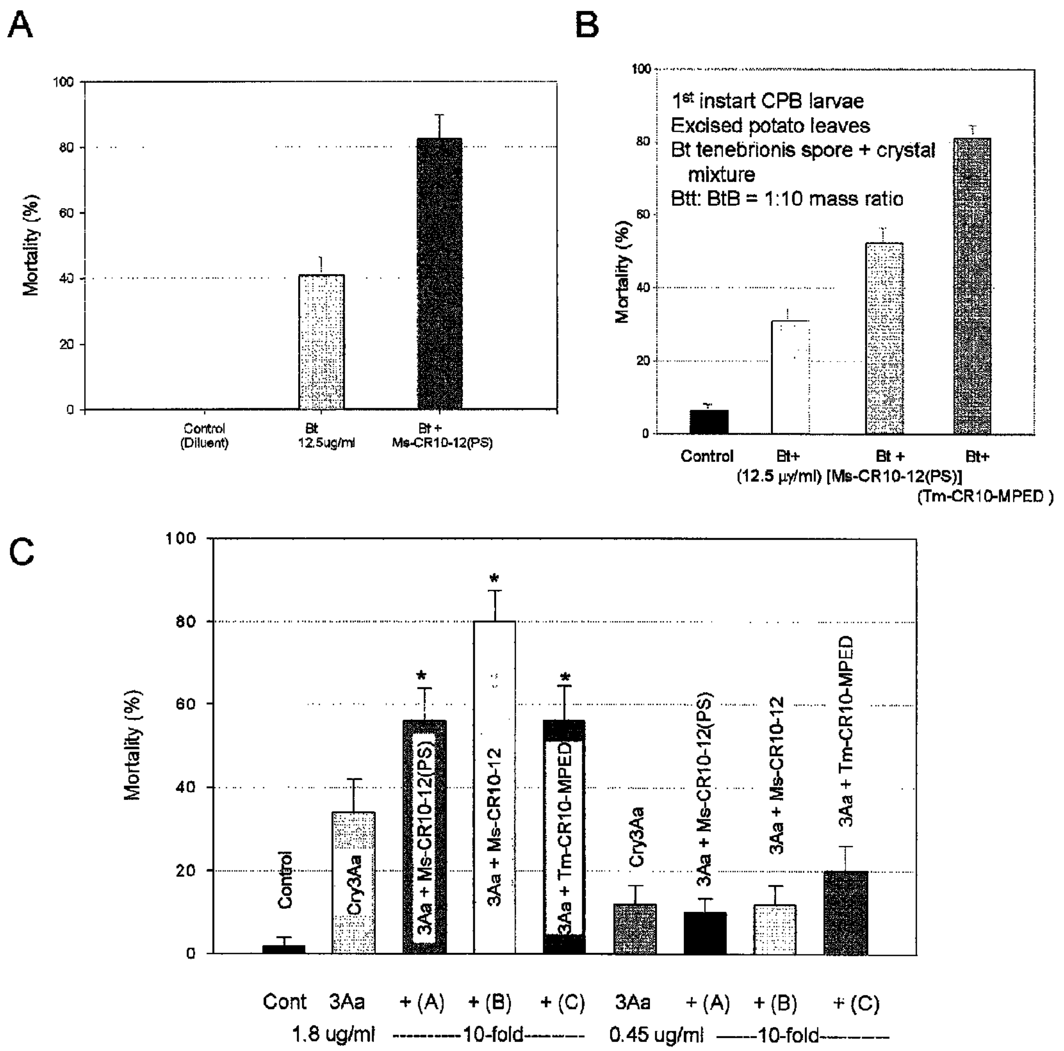

FIG. 2 illustrates enhancement of *Bt tenebrionis* spore and Cry3Aa crystal toxicity to CPB larvae by the cadherin peptides Ms-CR10-12, Ms-CR10-12(PS) (Panel A), Tm-CR10-12 and Ms-CR10-12(PS) (Panel B), and Ms-CRL0-12 and Tm-CR10-MPED (Panel C). In Panels A and C, Bt suspensions were weighed as a dried powder and mixed in diluent alone or with the cadherin peptides in a 1:10 Bt:Cadherin Peptide mass ratio. In Panel. C, the amount of Cry3Aa in the Btt spore crystal mixture was estimated by SDS-PAGE and scanning densitometry. The indicated amounts were mixed in diluent alone or with the indicated cadherin peptides.

Figure 3:
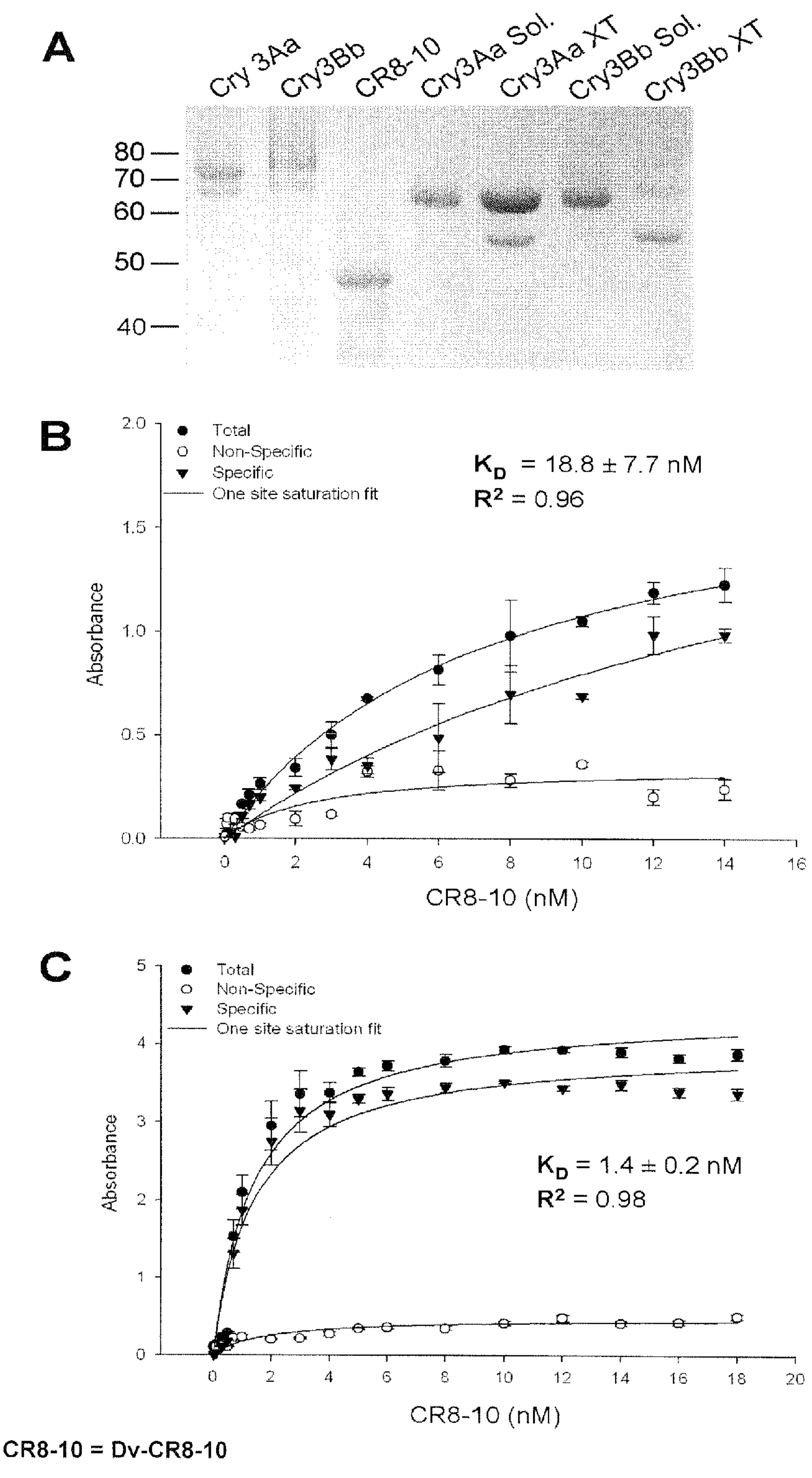

FIG. 3. SDS-PAGE of Cry3Aa, Cry3Bb and Dv-CR8-10 (or CR8-10) peptide (Panel A) and binding saturation of biotinylated Dv-CR8-10 peptide to Cry3 toxins (Panels B and C). Panel A, lanes: Cry3Aa (crystals), Cry3Bb (crystal inclusions), and Dv-CR8-10 (crystal inclusions), solubilized Cry3Aa and Cry3Bb before and after chymotrypsin treatment (designated with XT). In Panels B and C: binding of biotinylated Dv-CR-8-10 to Cry3Aa or Cry3Bb protein was determined using an ELISA-based binding assay. Microtiter plates were coated with chymotrypsin-treated Cry3Aa or Cry3Bb and then incubated with increasing various concentrations of biotinylated Dv-CR8-10 peptide. Bound biotinylated Dv-CR8-10 peptide was detected with a Streptavidin-HRP conjugate and substrate. Non-specific binding was determined in the presence of 1000-fold excess unlabeled CR8-10 peptide. Each data point is the mean of two experiments done in duplicate. Error bars depict standard deviation. Binding affinities (Kd) were calculated based on specifically bound biotinylated Dv-CR8-10 peptide using a one site saturation binding equation.

Figure 4:
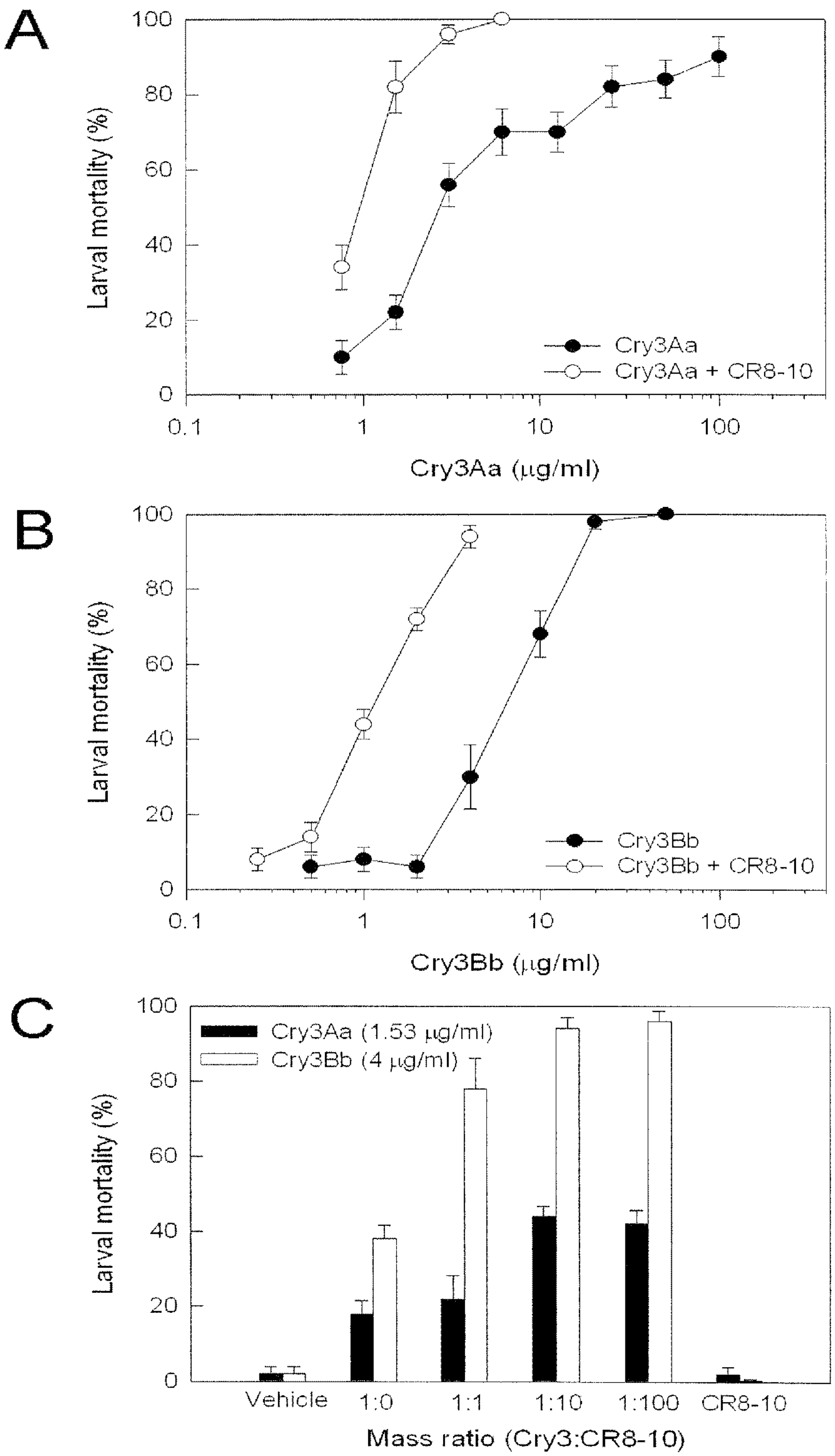

FIG. 4. Dv-CR8-10 peptide enhances Cry3Aa and Cry3Bb toxicity to CPB larvae. Suspensions of Cry3Aa crystals (Panel A) or Cry3Ba (Panel B) inclusions without or with Dv-CR8-10 inclusions at a toxin:peptide mass ratio of 1:10 were sprayed onto excised potato leaves. In Panel C, treatments consisted of Cry3Aa or Cry3Bb alone, or with varying toxin:peptide mass ratios of Dv-CR8-10 peptide. Buffer and CR8-10 peptide at 400 μg/ml were not toxic to the larvae. Each bioassay consisted of 5 CPB larvae per Petri dish with 10 cups per treatment. Larval mortality was scored on Day 3. Concentrations are expressed as micrograms Cry protein per ml suspension. Each data point represents data for the mean±standard error from a bioassay with 50 larvae per dose.

Figure 5:
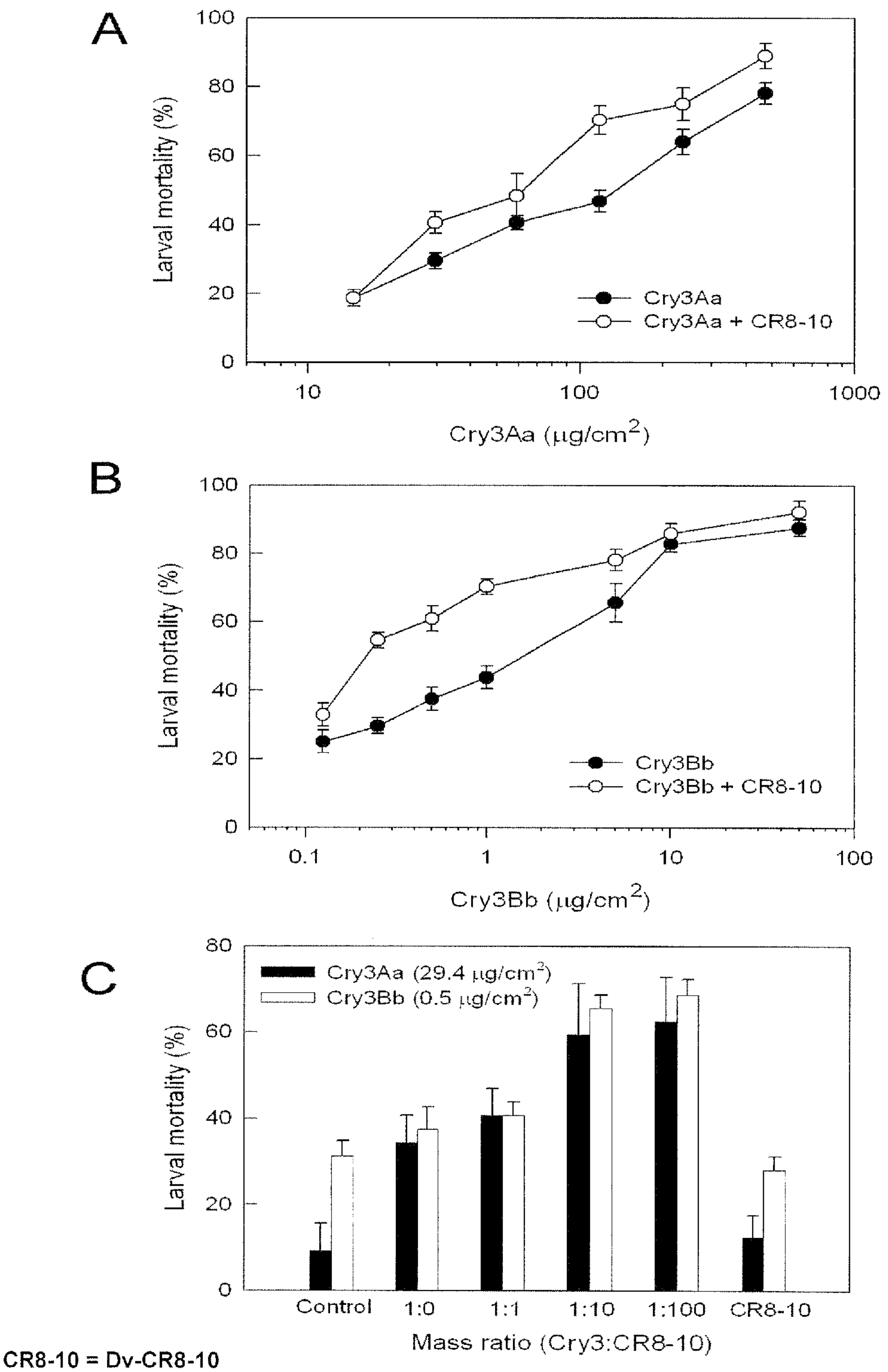

FIG. 5. Comparison of Cry3Aa and Cry3Bb toxicity to SCRW larvae without and with Dv-CR8-10 peptide. Suspensions of Cry3Aa crystals (Panel A) or Cry3Ba (Panel B) inclusions without or with Dv-CR8-10 inclusions at a toxin:peptide mass ratio of 1:10 were fed to $1^{st}$ instar SCRW larvae in a surface overlay bioassay. Panel C shows the enhancement effects of increasing ratios of Dv-CR8-10 peptide in Cry3Aa or Cry3Bb suspensions. No toxicity was observed when treated with Dv-CR8-10 peptide alone. Mortality was scored on day 7. Each data point represents data for the mean±standard error from a bioassay with 32 larvae per dose.

Figure 6:
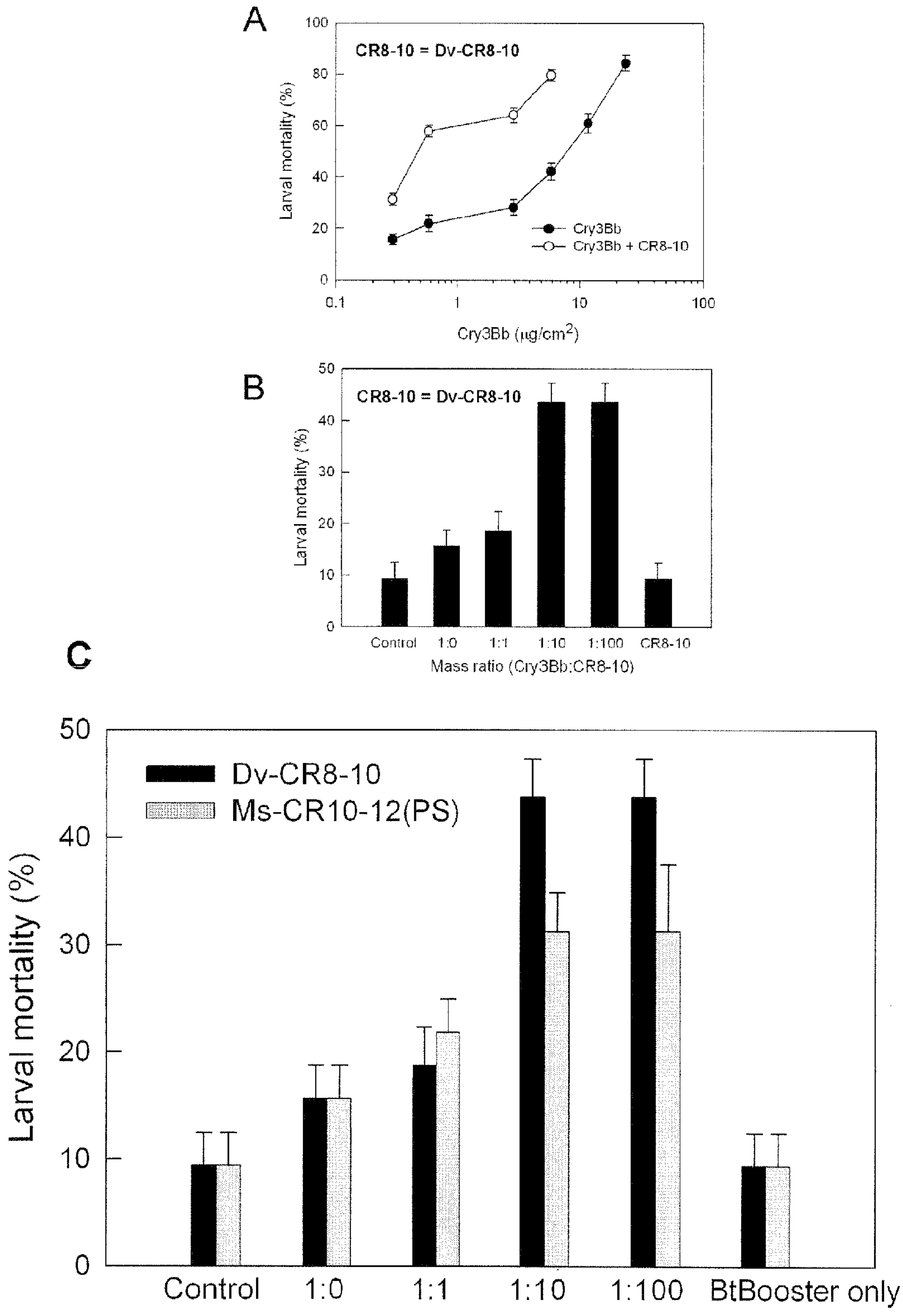

FIG. 6. Dv-CR8-10 peptide enhancement of Cry3Bb toxicity to WCRW larvae. Larvae were exposed to diet treated with Cry3Bb crystals alone or Cry3Bb plus Dv-CR8-10 inclusions at fixed 1:10 (Panel A) or varying toxin:peptide ratios (Panel B). In Panel B the Cry3Bb concentration was 1.0 $\mu g/cm^2$. Mortality was scored on day 6. Each data point represents data for the mean±standard error from a bioassay with 32 larvae per dose. (Panel C) Diet surface bioassay showing enhancement of Cry3Bb (@ 1 $\mu g/cm^2$ well) with 1:10 and 1:100 ratio of Dv-CR8-10 or Ms-CR10-12(PS) against 1st instar western corn rootworm. Dv-CR8-10 shows better enhancement of toxicity than Ms-CR10-12(PS). No toxicity was observed when treated with Dv-CR8-10 or Ms-CR10-12(PS) alone (@ 100 $\mu g/cm^2$). Bioassay result was scored on 6th day after treatment.

Figure 7:
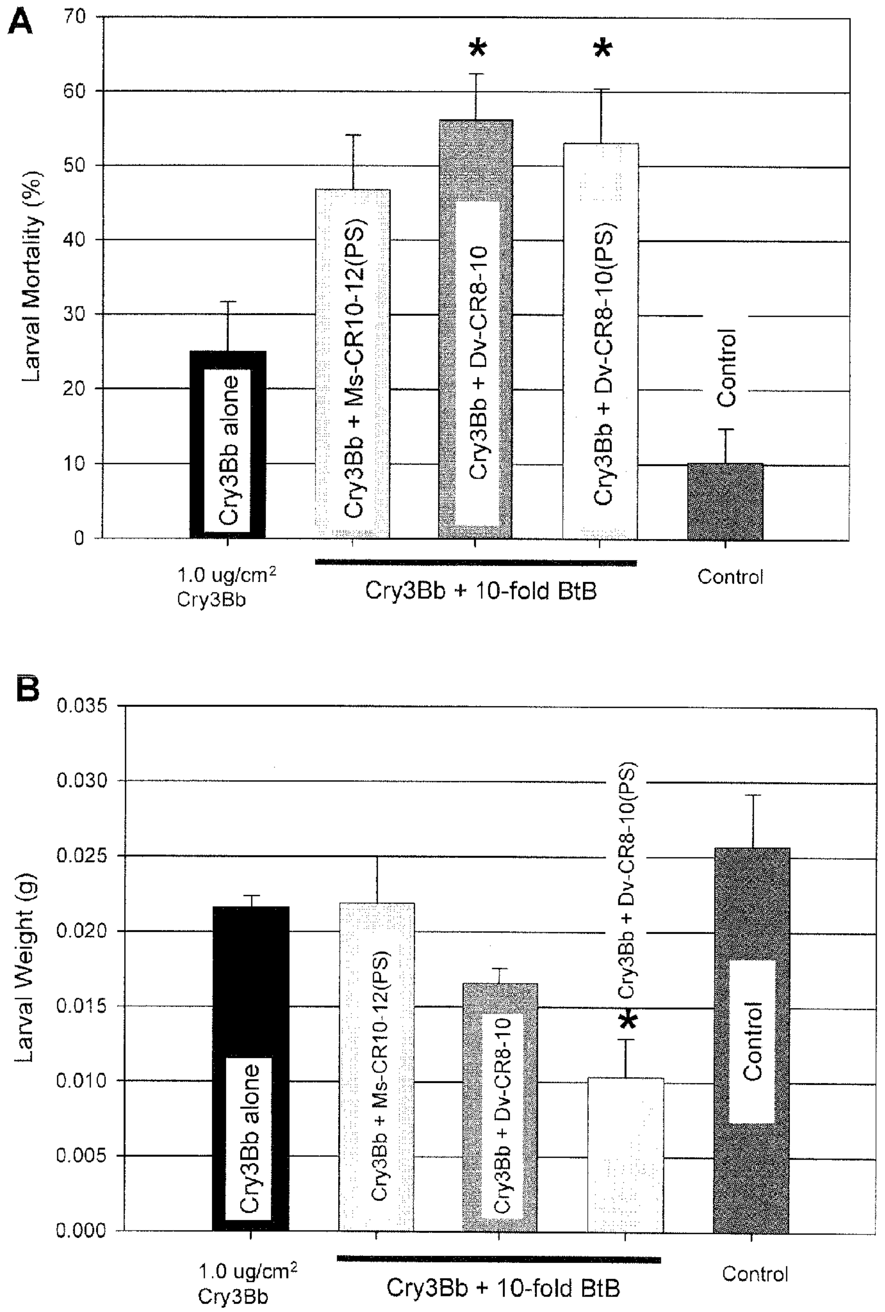

FIG. 7. Diet surface treatment bioassay with neonate western corn rootworm (WCRW). Sample size: 16 larvae/rep×2 rep/treatment. One $\mu g/cm^2$ Cry3Bb was applied alone or with 10-fold mass ratio of the different BtBs on diet surface. Soluble BtBs were purified with Ni-column. Cry3Bb was partially solubilized with 20 mM $Na_2CO_3$ pH 10.0. Bioassay was scored on Day 6. (Panel A) Mortality data. (Panel B) Larval weight data.

BRIEF DESCRIPTION OF THE SEQUENCES

SEQ ID NO:1 provides the combined polynucleotide/amino acid sequences of Ms-CR10-12 (BtB4).

SEQ ID NO:2 provides the protein sequence from SEQ ID NO:1 (BtB4).

SEQ ID NO:3 provides the combined polynucleotide/amino acid sequences of Ms-CR10-12(PS) proteinase stabilized CR10-12. The protein/peptide/polypeptide of SEQ ID NO:3 is also referred to as BtB5.

SEQ ID NO:4 provides the protein sequence from SEQ ID NO:3 (BtB5).

SEQ ID NO:5 is the Dv-CR8-10/CR8-10 nucleotide sequence from WCRW cadherin with EcoRI, HindIII cloning sites.

SEQ ID NO:6 provides the combined polynucleotide/amino acid sequences of Dv-CR8-10/CR8-10 nucleotide and amino acid sequence from the WCRW cadherin. The polypeptide/protein of SEQ ID NO:6 is also known as BtB7.

SEQ ID NO:7 provides the protein sequence from SEQ ID NO:6 (BtB7).

SEQ ID NO:8 is the Tm-CR10-MPED nucleotide sequence encoding the last cadherin repeat (CR) and membrane proximal extracellular domain (MPED) of *Tenebrio molitor* cadherin. The ends (underlined) contain Nde1 and Xho1 sites for cloning into a *E. coli* expression vector pET30A. A 6× his coding sequence was included at the C-terminus.

SEQ ID NO:9 provides the combined nucleotide and amino acid sequences of the Tm-CR10-MPED cadherin fragment from the *Tenebrio molitor* cadherin. The coding region includes the last cadherin repeat (CR) and membrane proximal extracellular domain (MPED) of the *Tenebrio molitor* cadherin. The 5' and 3' ends contain Nde1 and Xho1 sites for cloning into an *E. coli* expression vector. A 6× his coding sequence was included at the C-terminus. This region was cloned into pET30a and expressed in. *E. coli.*

SEQ ID NO:10 provides the protein sequence from SEQ ID NO:9.

SEQ ID NO:11 provides the combined polynucleotide/amino acid sequences of Dv-CR8-10(PS)—the Proteinase Stabilized Dv-CR8-10 from the WCRW cadherin. The polypeptide of SEQ ID NO:11 is also called BtB8.

SEQ ID NO:12 provides the protein sequence from SEQ ID NO:11 (BtB8).

DETAILED DISCLOSURE OF THE INVENTION

The subject invention relates in part to the discovery that a fragment from a cadherin of the western corn rootworm enhances Cry3 toxicity to larvae of naturally susceptible species. The subject invention also relates in part to the discovery that a cadherin fragment from a beetle enhances Cry3Aa and Cry3Bb toxicity to coleopteran larvae, particularly those in the family Chrysomelidae.

The cadherin repeat (CR) 8-10 of *Diabrotica virgifera virgifera* was expressed in *E. coli* as an inclusion body. Larvae ingesting CR10-12 inclusions had increased susceptibility to Cry3Aa or Cry3Bb toxins. The Cry3 toxin-enhancing effect of CR8-10 was demonstrated for Colorado potato beetle (*Leptinotarsa decimlineata*), southern corn rootworm (*D. undecimpunctata howardi*) and western corn rootworm (*D. virgifera virgifera*). The extent of Cry3 toxin enhancement, which ranged from 3- to 8-fold, has practical applications for insect control.

The region spanning CR10-12 of the WCRW cadherin (Siegfried et al. 2007) was cloned and expressed in *E. coli*. This cadherin fragment significantly enhanced the toxicities of Cry3Aa and Cry3Bb toxins to CPB and rootworms.

The western corn rootworm midgut cadherin (Sayed et al., 2007) was used as a template to design a cadherin fragment that includes a potential toxin binding site. The designed CR8-10 peptide includes the predicted binding site $^{1311}$SSLNVTVN$^{1318}$ which has similarity to Cry1A toxin binding region 2 (TBR 2) of *M. sexta* cadherin (Sayed et al., 2007). The WCRW cadherin and the CR8-10 cadherin peptide do not contain a clear match to TBR 3 (GVLTLNIQ; residues 1416-1423) of *M. sexta* cadherin (Chen et al., 2007). This is significant because when Chen et al. (Chen et al., 2007) deleted the critical TBR 3, their cadherin fragment did not bind or enhance Cry1A toxicity. Three cadherin repeats were included in our cadherin peptide, in part because of observations that CR10-12 of *M. sexta* cadherin has greater Cry1A toxin binding and enhancing properties than CR12 alone.

The CR8-10 cadherin fragment from WCRW increased the potency of Cry3Aa and Cry3Bb proteins between three and about eight-fold against CPB and two rootworm species. This level of potentiation is comparable and in some cases greater than our published reports of cadherin fragment enhancement of Cry1Ab toxicity to *M. sexta* and Cry4Ba toxicity to *A. gambiae* (Chen et al., 2007; Hua et al., 2008). In these reports the cadherin fragments consisted of terminal CR and membrane proximal extracellular domains derived from the respective species and both cadherin fragments bound toxin. The toxin-enhancing cadherin fragments of those studies also bound Cry toxin. Soberon et al. (Soberon et al., 2007) provide an explanation for how cadherin fragments are involved in Cry1Ab toxicity. The CR12 fragment induces formation of a pre-pore Cry1Ab-cadherin oligomer, a critical step in intoxication process (Jimenez-Juarez et al., 2008).

There is practical importance of a three to eight-fold level of synergy on field performance of biopesticides. In the case of susceptible CPB larvae and 'high-dose' Cry3Aa expression in transgenic Bt Newleaf potato, a 3-fold enhancement of Cry3Aa toxicity can have some impact on inhibition of insects. In addition, where weekly sprays of a microbial biopesticide are required due to short field half-life and tolerance in older larvae (Zhender and Galertner, 1989), a three-fold enhancement of Cry3Aa toxicity may result in highly efficacious control of CPB.

*Diabrotica* species are major pests of corn in the U.S. significantly impacting corn grown for food and ethanol production, and adult *D. undecimpunctata howardi* (SCRW or cucumber beetle) is an important insect pest of cucurbits. The LC50 value (1.6 $\mu g/cm^2$) we determined for SCRW larvae is considerably less than the 61.5 $\mu g/cm^2$ previously reported (Johnson et al., 1993). The Cry3Bb $LC_{50}$ (5 $\mu g/cm^2$) against WCRW is within the 0.7 to 9.2 $\mu g/cm^2$ values calculated for laboratory and field populations of WCRW (Siegfried et al. 2007). The MON 863 cultivar of Bt maize (also called Yieldguard Rootworm) expresses a modified Cry3Bb, that has 8-fold increased toxicity relative to Cry3Bb, yet some western and southern corn rootworms survive on MON 863 corn. Although factors such as feeding behavior and environmental conditions can impact rootworm survival, a peptide synergist that increases Cry3Bb potency could lead to improved rootworm control.

Based on current data, the BtBs could enhance the following (but not limited to) examples of coleopteran-active Bt toxins (obtained from the online Bt specificity database: world wide web glfc.forestry.ca/bacillus/). The following Bt toxins are known to have toxicity against Colorado potato beetle: Cry1Ba, Cry1Ia, Cry3Aa, Cry3Ba, Cry3Bb, Cry3Ca, Cry7Aa, Cry8Aa, Cry8Bb, and Cry8Bc. The following Bt toxins are known to have toxicity against corn rootworm in general: Cry3Aa, Cry3Bb, Cry8Bb, Cry8Bc, Cry34Aa+Cry35Aa, Cry34Ab+Cry35Ab, Cry34Ac+Cry34Ab, Cry34Ba+Cry35Ba and Cry36Aa. The following Bt toxins are known to have toxicity against Japanese beetle: Cry8Ba, Cry8Da, Cry23Aa, and Cry37Aa. Various other *Bacillus thuringiensis* Cry proteins can be used with BtB polypeptides of the subject invention. See Crickmore et al. (1998) (world wide web website lifesci.sussex.ac.uk/home/Neil_Crickmore/Bt/) for a list of B.t. toxins.

The subject polypeptides and protein toxins can be "applied" or provided to contact the target insects in a variety of ways. For example, transgenic plants (wherein the protein is produced by and present in the plant) can be used and are well-known in the art. Expression of the toxin genes can also be achieved selectively in specific tissues of the plants, such as the roots, leaves, etc. This can be accomplished via the use of tissue-specific promoters, for example. Spray-on applications are another example and are also known in the art. The subject polypeptides/proteins can be appropriately formulated for the desired end use, and then sprayed (or otherwise applied) onto the plant and/or around the plant/to the vicinity of the plant to be protected—before an infestation is discovered, after target insects are discovered, both before and after, and the like. Bait granules, for example, can also be used and are known in the art. Various combinations of approaches are discussed in WO 2005/070214 A2, US-2005-0283857-A1, and U.S. Pat. No. 7,396,813.

The subject proteins can be used to protect practically any type of plant from damage by an insect. Examples of such plants include maize, sunflower, soybean, cotton, canola, rice, sorghum, wheat, barley, vegetables, ornamentals, peppers (including hot peppers), sugar beets, fruit, and turf, to name but a few.

As stated herein, polypeptides (together with a Cry protein) can inhibit one or more Coleopteran pests including the following. (The following can also be used as a source of the insect cadherin ectodomain.) Such insects include:

*Anthonomus grandis*, boll weevil
*Bothyrus gibbosus*, carrot beetle
*Chaetocnema pulicaria*, corn flea beetle
*Colaspis brunnea*, grape colaspis
*Cyclocephala borealis*, northern masked chafer (white grub)
*Cyclocephala immaculata*, southern masked chafer (white grub)
*Diabrotica longicornis barberi*, northern corn rootworm
*Diabrotica undecimpunctata howardi*, southern corn rootworm
*Diabrotica virgifera virgifera*, western corn rootworm
*Eleodes, Conoderus*, and *Aeolus* spp., wireworms
*Epilachna varivestis*, Mexican bean beetle
*Hypera punctata*, clover leaf weevil
*Lissorhoptrus oryzophilus*, rice water weevil
*Melanotus* spp., wireworms
*Oulema melanopus*, cereal leaf beetle
*Phyllophaga crinita*, white grub
*Phylotreta* spp., flea beetles including canola flea beetle
*Popillia japonica*, Japanese beetle
*Sitophilus oryzae*, rice weevil
*Sphenophorus maidis*, maize billbug
*Zygogramma exclamationis*, sunflower beetle In light of and having the benefit of the subject application, variants of novel BtBs of the subject invention (e.g. those derived from *Diabrotica* and *Tenebrio* cadherins) can be constructed using techniques that are known in the art.

It will be recognized by those skilled in the art that the DNA sequences may vary due to the degeneracy of the genetic code and codon usage. All DNA sequences which code for exemplified and/or suggested peptides (and proteins) are included. The subject invention also includes polynucleotides having codons that are optimized for expression in plants, including any of the specific types of plants referred to herein. Various techniques for creating plant-optimized sequences are know in the art.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that exemplified sequences can be used to identify and isolate additional, non-exemplified nucleotide sequences that will encode functional equivalents to the DNA sequences, including those that encode amino acid sequences having at least 85% identity thereto and having equivalent biological activity, those having at least 90% identity, and those having at least 95% identity to a novel BtB polypeptide of the subject invention. Other numeric ranges for variant polynucleotides and amino acid sequences are provided below (e.g., 50-99%). Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) *Nucl. Acids. Res.* 25:3389-3402. When utilizing BLAST and Gapped BLAST programs, the default parameters of the respective programs (NBLAST and XBLAST) are used. See ncbi.nih.gov website.

Polynucleotides (and the peptides and proteins they encode) can also be defined by their hybridization characteristics (their ability to hybridize to a given probe, such as the complement of a DNA sequence exemplified herein). Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169-170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with $^{32}P$-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20-25° C. below the melting temperature (Tm) of the DNA hybrid in 6×SSPE, 5× Denhardt's solution, 0.1% SDS, 0.1 mg/ml denatured DNA. The melting temperature is described by the following formula from Beltz et al. (1983).

$$Tm=81.5° \text{ C.}+16.6 \text{ Log [Na+]}+0.41(\% \, G+C)-0.61(\% \text{ formamide})600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5× Denhardt's solution, 0.1% SDS, 0.1 mg/ml denatured DNA. Tm for oligonucleotide probes was determined by the following formula from Suggs et al. (1981):

$$Tm \text{ (° C.)}=2 \text{ (number } T/A \text{ base pairs)}+4\text{(number } G/C \text{ base pairs)}$$

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash)

In general, salt and/or temperature can be altered to change stringency. With a labeled DNA fragment of greater than about 70 or so bases in length, the following can be used:

1 or 2×SSPE, room temperature 1 or 2×SSPE, 42° C.

0.2× or 1×SSPE, 65° C.

0.1×SSPE, 65° C.

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide and amino acid sequences of the invention can be used in the same manner as the exemplified sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage. In some embodiments, the identity and/or similarity can also be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid identity/similarity and/or homology will be highest in critical regions of the protein that account for biological activity and/or are involved in the determination of three-dimensional configuration that ultimately is responsible for the biological activity. In this regard, certain amino acid substitutions are acceptable and can be expected if these substitutions are in regions that are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. The following table provides a listing of examples of amino acids belonging to each class.

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made.

All patents, patent applications, provisional applications, and publications referred to or cited herein are incorporated by reference in their entirety to the extent they are not inconsistent with the explicit teachings of this specification. Unless specifically indicated or implied, the terms “a”, “an”, and “the” signify “at least one” as used herein. Following are examples that illustrate procedures for practicing the invention. These examples should not be construed as limiting. All percentages are by weight and all solvent mixture proportions are by volume unless otherwise noted.

EXAMPLE 1

Cloning and Expression of CR8-10 of the Western Corn Rootworm Cadherin-Like Protein A DNA fragment encoding amino acids 961-1329 (corresponding to CR8-10 sequence) of the *D. virgiftra virgifera* cadherin-like protein (GI:156144975) was synthesized by GenScript Corp. (Piscataway, N.J.) and the synthetic gene was inserted between the Nde I and HindIII restriction enzyme sites of an expression vector, pET30a(+) (Novagen, Madison, Wis.). The coding sequence and clone orientation were confirmed by sequencing (Molecular Genetics Instrumentation Facility at University of Georgia). The pET construct was transformed into *E. coli* strain BL21(DE3)/pRIL (Stratagene, La Jolla, Calif.), and positive clones were selected on LB plates containing kanamycin and chloramphenicol. The CR8-10 peptide was overexpressed in *E. coli* as inclusion bodies. The expression and purification protocol for the truncated cadherin fragment was as described in a previous paper (Chen et al., 2007). The inclusion body form was prepared as a suspension in sterile deionized water. Total protein was measured by Bio-Rad protein assay using bovine serum albumin (BSA) as standard (Bradford, 1976). One microgram of each cadherin peptide was analyzed by sodium dodecyl sulfate-15% polyacrylamide gel electrophoresis (SDS-15% PAGE) with Coomassie brilliant blue R-250 staining. Specific concentration of target protein, such as toxin or the cadherin peptide in total protein was determined from Coomassie-stained gel by gel image analyzer (Alpha Innotech, San Leandro, Calif.) using bovine serum albumin (BSA) as standard.

EXAMPLE 2

Culture of Bt Tenebrionis and Purification of Cry3Aa Crystals

*Bt tenebrionis* strain was grown in peptone glucose salts medium (Brownbridge and Margalit, 1986) until sporulation and cell lysis. The spore crystal mixture was harvested by centrifugation, suspended in 0.1M NaCl, 2% Triton X-100, 20 mM Bis-Tris, pH6.5 and sonicated. Spores and crystals were pelleted by centrifugation at 12,000 g for 10 min, washed twice with 0.5M NaCl, followed by a single wash in distilled water. Cry3Aa crystals were purified according to (Slaney et al., 1992) and the final Cry3Aa protein concentration was determined based on band density on SDS-15% PAGE, using BSA as standard. Crystals were stored at 4° C. until used for experimentation.

EXAMPLE 3

Cloning and Expression of the Cry3Bb Gene

The Cry3Bb coding region was cloned by PCR using total DNA extracted from the Bt biological insecticide Raven (Ecogen, Inc. Langhorne, Pa.) as template with primers Cry3Bb/FWD (CAGGTCTAGAGTTATGTATTATGATAA-GAATGGG) and Cry3Bb/REV (TAAACTCGAGTTA-CAATTGTACTGGGATAAATTC). The PCR amplified cry3Bb gene was cloned into pGEM-T Easy vector (Promega, Madison, Wis.), and then subcloned between the Xba I and XhoI sites of the pET30a(+). The clone called Cry3Bb/pET was transformed into *E. coli* strain BL21-CodonPlus (DE3)/pRIL (Stratagene, LaJolla, Calif.). The coding sequence and clone orientation were confirmed by sequencing. The expression and purification protocol for the Cry3Bb protein inclusion bodies was as described above for CR8-10 peptide.

EXAMPLE 4

Insect Bioassays

Adult CPB were obtained from the New Jersey Department of Agriculture (Trenton, N.J.). A CPB colony was maintained on containerized potato plants in an environmental chamber at 25° C. and 70% relative humidity with a photoperiod of 16 hrs light: 8 hrs dark. Neonate CPB larvae were fed fresh potato leaves for 5 hrs before bioassay. Suspensions (30 ml) of Cry3 crystals or crystals plus CR8-10 inclusions prepared in diluent [0.12% v/v Kinetic (Helena Chemical Co, Collierville, Tenn.)] plus 0.12% v/v commercial-grade polyethylene and octyl phenol polyethoxy ethanol spreader-sticker (Southern Agricultural Insecticides, Inc., Boon, N.C.) in tap water], were sprayed on potato leaves and the leaves were air-dried in a fume hood for 15 min. 10 larvae were applied to treated leaves in a petri dish. Each bioassay was conducted with 50 larvae per dose.

Eggs of southern corn rootworm (SCRW) and western corn rootworm (WCRW) were obtained from French Agricultural Research, Inc. (Lamberton, Minn.) and incubated at 25° C. for 8 days and 16 days until hatching, respectively. Molten SCRW artificial diet (Bio-Serv, Frenchtown, N.J.) was adjusted to pH 7.0 (according to the manufacturer) for SCRW bioassay and to pH 9.0 for WCRW bioassay with KOH and then applied onto 128-well bioassay tray (C-D International, Pitman, N.J.). Cry3 crystals or crystals with CR8-10 inclusions were serially diluted with sterile deionized water and then overlaid onto the diet surface and air-dried. One newly hatched larva was transferred into each well; the trays were sealed with perforated lids (C-D International, Pitman, N.J.) and then covered with brown paper to provide a dark environment. Each bioassay was conducted with 16 larvae per replicate and two replicates per dose. The trays were incubated at 28° C. for 6 days for WCRW or 7 days for SCRW before mortality counts were scored. Bioassays were repeated at least twice.

EXAMPLE 5

Results

In this study, the CR8-10 region of WCRW cadherin (Sayed et al., 2007) was over-expressed in *E. coli* and tested for the ability to enhance Cry3Aa and Cry3Bb toxicity to CPB and rootworm larvae. The CR8-10 region is homologous to toxin-enhancing regions from *M. sexta* and *A. gambiae* cadherins and contains a predicted toxin binding region (Sayed et al., 2007). The native WCRW coding sequence was optimized for *E. coli* expression, and most of the $C_pG$ sequences in the native cadherin sequence were removed to decrease potential DNA methylation in planta. The synthetic CR8-10 peptide of 377 amino acid residues has an initiation methionine, a C-terminal 6 histidine tag, and a molecular size of 42,814 Da. Inclusion bodies isolated from recombinant *E. coli* were composed of the expected 45-kDa protein, plus lesser amounts of two about 30-kDa peptides (FIG. 3A).

Cry3Aa crystals were prepared from *Bt tenebrionis*, and Cry3Bb inclusions were isolated from recombinant *E. coli* for testing in insect bioassays with CR8-10 inclusions. The Cry3Aa crystals and Cry3Bb crystals were composed of the expected 73- and 75-kDa protoxin-sized proteins (FIG. 3A). Leaflets of potato were sprayed with suspensions of Cry3 crystals alone or crystals with CR8-10 inclusions, air dried and fed to first instar potato beetle larvae. The calculated $LC_{50}$ mortality values were 4.4 μg Cry3Aa/ml and 6.5 μg Cry3Bb/ml (Table 1; FIGS. 4A and B). The addition of CR8-10 inclusions at a 1:10 mass ratio of Cry3:CR8-10 to the crystal suspensions reduced the Cry3Aa and Cry3Bb $LC_{50}$ values 3.3-fold and 6-fold, respectively. To determine the extent that CR8-10 could enhance a low dose of toxin, we added increasing amounts of CR8-10 inclusions to a Cry3 crystal concentration predicted to cause about 20% larval mortality. As seen in FIG. 4C, the enhancement effect reached a plateau at a 1:10 (Cry protein:CR8-10) mass ratio. The CR8-10 peptide enhanced the low Cry3Bb dose to a greater extent than Cry3Aa.

The different and expected insecticidal properties of Cry3Aa and Cry3Bb were detected in our bioassays against SCRW. Whereas Cry3Bb is toxic to southern corn rootworms (SCRW) *Diabrotica undecimpactata howardi* (Coleoptera: Chrysomelidae), Cry3Aa has lower toxicity to this pest (FIG. 5A); c.f. (Donovan et al., 1992; Slaney et al., 1992). The ability of CR8-10 peptide to enhance Cry3Aa and Cry3Bb toxicity to SCRW was tested using a 1:10 (Cry3:CR8-10) mass ratio. The addition of CR8-10 to Cry3Aa reduced the $LC_{50}$ value about 1.7-fold. As seen in FIG. 5A, the highest dose of Cry3Aa and Cry3Aa plus CR8-10 killed less than 100% of the larvae. Cry3Bb was about 100-fold more toxic than Cry3Aa to SCRW larvae in diet overlay bioassays (Table 1, FIG. 5B). The addition of Cry8-10 inclusions increased Cry3Aa and Cry3Bb toxicity to SCRW larvae (Table 1) and the mass ratio 1:10 (Cry3:CR8-10) was optimal for toxicity enhancement.

Since Cry3Bb, but not Cry3Aa, is active against WCRW, we tested the ability of CR8-10 to enhance Cry3Bb toxicity. As seen in FIG. 5A, CR8-10 enhanced Cry3Bb toxicity at each toxin dosage tested. The $LC_{50}$ for Cry3Bb was 5.2 $\mu g/cm^2$ and the $LC_{50}$ for Cry3Bb plus a 1:10 toxin to cadherin fragment ratio was 0.7 $\mu g/cm^2$ representing a 7.9-fold-fold enhancement by CR 8-10 peptide. Maximal enhancement of Cry3Bb toxicity WCRW larvae occurred with a 1:10 Cry3Bb: CR8-10 mass ratio (FIG. 6B).

EXAMPLE 6

Further Results

In this study additional BtBoosters were tested in combination with beetle-active Bt (*B. thuringiensis* subsp. *tenebrionis*), which produces Cry3Aa toxins against Colorado Potato Beetle (CPB) larvae. After initial dose response bioassays, a Bt dose that caused about 40% mortality (12.5 μg/ml) was chosen for further bioassays using various BtBooster™ constructs (TmCad, a *T. mollitor*-derived cadherin peptide; BtB5 and BtB6, *M. sexta*-derived cadherin peptides). Several preliminary bioassays were performed, and the results are shown in FIG. 2. The data show that addition of BtB5, BtB6, or TmCad increased the toxicity of *Bt tenebrionis* against CPB. Statistical analysis by pair-wise Chi-square analysis showed that the enhancements were significant ($P<0.05$).

These results are very interesting because it shows that a *lepidoptera*-derived BtBooster™ (i.e. BtB5 and BtB6) and a coleopteran-derived BtBooster (i.e. TmCad) can be combined with a beetle-active Bt to elicit a synergistic effect.

EXAMPLE 7

Still Further Results

The ability of BtB5 to enhance Cry3Bb toxicity to WCRW larvae was demonstrated in a diet surface bioassay against $1^{st}$ instar WCRW larvae. The CR8-10 from WCRW was included for comparison. FIG. 2 shows the results of a diet surface bioassay showing enhancement of Cry3Bb (at 1 μg per well) with 1:10 and 1:100 ratios of CR8-10 or BtB5 against 1st instar WCR. CR8-10 shows better enhancement of toxicity than BtB5. No toxicity was observed when treated with WCR8-10 or BtB5 alone (at 100 ug per well). Bioassay result was scored on 6th day after treatment.

EXAMPLE 8

Control of Additional Coleopteran Insects with Additional Cry Proteins

The subject invention can also be extended to other Cry proteins. For example, BtBs of the subject invention can be used in combination with Cry34/35 proteins to enhance control of corn rootworms. In some specific embodiments of these embodiments, BtB5, BtB7, and BtB8 enhance Cry34/Cry35 for inhibiting corn rootworms. In addition, in some preferred embodiments, BtB5, BtB7, and BtB8 can be used with Cry8 proteins for controlling grubs, particularly white grubs.

TABLE 1

Effect of CR8-10 peptide on Cry3Aa and Cry3Bb toxicity to CPB, SCRW and WCRW larvae[a]

| Treatment | Insect | $LC_{50}$ | Relative Toxicity | Control Mortality (% ± SE) | CR8-10 Mortality (% ± SE) |
|---|---|---|---|---|---|
| Cry3Aa[b] | CPB | 3.21 (2.17-4.44) | — | 3.0 ± 3.0 | |
| Cry3Aa + CR8-10[d] | CPB | 0.96 (0.79-1.12) | 3.3 | 3.0 ± 3.0 | 4.0 ± 2.0 |
| Cry3Bb[c] | CPB | 6.54 (5.54-7.86) | — | 6.0 ± 3.5 | |
| Cry3Bb + CR8-10 | CPB | 1.09 (0.88-1.35) | 6 | 6.0 ± 3.5 | 2.0 ± 2.0 |
| Cry3Aa | SCRW | 91.81 (61.95-134.12) | — | 12.5 ± 4.0 | |
| Cry3Aa + CR8-10 | SCRW | 56.79 (43.34-72.31) | 1.6 | 12.5 ± 4.0 | 12.5 ± 3.3 |
| Cry3Bb | SCRW | 1.18 (0.80-1.71) | — | 12.5 ± 4.0 | |
| Cry3Bb + CR8-10 | SCRW | 0.26 (0.14-0.42) | 4.5 | 12.5 ± 3.3 | 12.5 ± 4.0 |
| Cry3Bb | WCRW | 5.18 (2.90-10.04) | — | 9.3 ± 3.1 | |
| Cry3Bb + CR8-10 | WCRW | 0.65 (0.24-1.21) | 7.9 | 9.3 ± 3.1 | 9.3 ± 3.1 |

[a]Results are 50% lethal doses ($LC_{50}$) (with 95% confidence intervals) and are expressed as micrograms of Cry protein per ml for CPB bioassays and micrograms of Cry protein per square centimeter of diet surface for SCRW and WCRW bioassays.
[b]Cry3Aa crystals were purified from a sporulated *Bt tenebrionis* culture.
[c]Cry3Bb inclusions were prepared from recombinant *E. coli*.
[d]Cry8-10 inclusions were isolated from *E. coli* expressing the CR8-10 region of WCRW cadherin.

REFERENCES

Belfiore, C. J., et al., 1994. A specific binding protein from *Tenebrio molitor* for the insecticidal toxin of *Bacillus thuringiensis* subsp. *tenebrionis*. Biochem Biophys Res Commun. 200, 359-64.

Bradford, M., 1976. A rapid and sensitive method for the quantitation of microgram quantities of protein utilizing the principle of protein-dye binding. Anal. Biochem. 72, 248-254.

Brownbridge, M., Margalit, J., 1986. New *Bacillus thuringiensis* strains isolated in Israel are highly toxic to mosquito larvae. J Invertebr Pathol. 48, 216-22.

Carroll, J., et al., 1997. Intramolecular proteolytic cleavage of *Bacillus thuringiensis* Cry3A delta-endotoxin may facilitate its coleopteran toxicity. Journal of Invertebrate Pathology. 70, 41-49.

Chen, J., et al., 2007. Synergism of *Bacillus thuringiensis* toxins by a fragment of a toxin-binding cadherin. Proc Natl Acad Sci USA. 104, 13901-6.

Donovan, W. P., et al., 1992. Characterization of two genes encoding *Bacillus thuringiensis* insecticidal crystal proteins toxic to Coleroptera species. Appl. Environ. Microbiol. 58, 3921-3927.

Galitsky, N., et al., 2001. Structure of the insecticidal bacterial delta-endotoxin Cry3Bb1 of *Bacillus thuringiensis*. Acta Crystallographica Section D-Biological Crystallography. 57, 1101-1109.

Gelernter, W., 2004. The rise and fall of *Bacillus thuringiensis tenebrionis*. Phytoparasitica. 32, 321324.

Hua, G., et al., 2004. Bt-R1a extracellular cadherin repeat 12 mediates *Bacillus thuringiensis* Cry1Ab binding and toxicity. J Biol. Chem. 279, 28051-28056.

Hua, G., et al., 2008. *Anopheles gambiae* cadherin AgCad1 binds the Cry4Ba toxin of *Bacillus thuringiensis israelensis* and a fragment of AgCad1 synergizes toxicity. Biochemistry. 47, 5101-10.

Jimenez-Juarez, N., et al., 2008. The pre-pore from *Bacillus thuringiensis* Cry1Ab toxin is necessary to induce insect death in *Manduca sexta*. Peptides. 29, 318-23.

Johnson, T. B., et al., 1993. Insecticidal Activity of Eg4961, a Novel Strain of *Bacillus-Thuringiensis* Toxic to Larvae and Adults of Southern Corn-Rootworm (Coleoptera, Chrysomelidae) and Colorado Potato Beetle (Coleoptera, Chrysomelidae). Journal of Economic Entomology. 86, 330-333.

Loseva, O., et al., 2002. Changes in protease activity and Cry3Aa toxin binding in the Colorado potato beetleL implications for insect resistance to *Bacillus thuringiensis* toxins. Insect Biochem. Mol. Biol. 32, 566-577.

Martinez-Ramirez, A. C., Real, M. D., 1996. Proteolytic processing of *Bacillus thuringiensis* CryIIIA toxin and specific binding to brush-border membrane vesicles of *Leptinotarsa decemlineata* (Colorado Potato Beetle). Pesticide Biochemistry and Physiology. 54, 115-122.

Ochoa-Campuzano, C., et al., 2007. An ADAM metalloprotease is a Cry3Aa *Bacillus thuringiensis* toxin receptor. Biochem Biophys Res Commun. 362, 437-42.

Sayed, A., et al., 2007. A novel cadherin-like gene from western corn rootworm, *Diabrotica virgifera virgifera* (Coleoptera: Chrysomelidae), larval midgut tissue. Insect Mol. Biol. 16, 591-600.

Slaney, A. C., et al., 1992. Mode of action of *Bacillus thuringiensis* toxin CryIIIA: An analysis of toxicity in *Leptinotarsa decemlineata* (Say) and *Diabrotica undecimpunctata howardi* barber. Insect Biochem. Mol. Biol. 22, 9-18.

Soberon, M., et al., 2007. Engineering modified Bt toxins to counter insect resistance. Science. 318, 1640-2.

Vaughn, T., et al., 2005. A method of controlling corn rootworm feeding using a *Bacillus thuringiensis* protein expressed in maize. Crop Science. 45, 931-938.

Walters, F. S., et al., 2008. An engineered chymotrypsin/cathepsin G site in domain I renders *Bacillus thuringiensis* Cry3A active against Western corn rootworm larvae. Appl Environ Microbiol. 74, 367-74.

Xie, R., et al., 2005. Single amino acid mutations in the cadherin receptor from *Heliothis virescens* affect its toxin binding ability to Cry1A toxins J. Biol. Chem. 280, 8416-8425.

We claim:

1. A method of inhibiting a rootworm, said method comprising providing said rootworm with a *Bacillus thuringiensis* Cry protein selected from the group consisting of a Cry 3 protein, a Cry34 protein together with a Cry 35 protein, a Cry 8 protein, and a Cry 36 protein and a polypeptide comprising a segment with at least 85% sequence identity with an coleopteran midgut cadherin ectodomain that binds said Cry protein.

2. The method of claim 1, wherein said polypeptide is selected from the group consisting of SEQ ID NOS:7, 12, and 10.

3. The method of claim 1 wherein said insect is of the genus *Diabrotica*.

4. The method of claim 1 wherein said insect is of the genus *Tenebrio*.

5. The method of claim 3 wherein said insect is *Diabrotica virgifera*.

6. The method of claim 5 wherein said ectodomain is the CR10-12 region.

* * * * *

SEQUENCE LISTING

```
<160> NUMBER OF SEQ ID NOS: 12

<210> SEQ ID NO 1
<211> LENGTH: 960
<212> TYPE: DNA
<213> ORGANISM: Manduca sexta
<220> FEATURE:
<221> NAME/KEY: CDS
<222> LOCATION: (1)..(957)

<400> SEQUENCE: 1

atg cac ttg gag cgg ata tcg gcg act gac ccg gac gga ctc cac gcg       48
Met His Leu Glu Arg Ile Ser Ala Thr Asp Pro Asp Gly Leu His Ala
1               5                   10                  15

ggc gtc gtc acc ttc caa gtg gta ggc gat gag gaa tca caa cgg tac       96
Gly Val Val Thr Phe Gln Val Val Gly Asp Glu Glu Ser Gln Arg Tyr
            20                  25                  30

ttt caa gta gtt aac gat ggc gcg aac ctc ggc tcg ttg agg tta ctg      144
Phe Gln Val Val Asn Asp Gly Ala Asn Leu Gly Ser Leu Arg Leu Leu
        35                  40                  45

caa gcc gtt cca gag gag atc agg gag ttc cgg ata acg att cgc gct      192
Gln Ala Val Pro Glu Glu Ile Arg Glu Phe Arg Ile Thr Ile Arg Ala
    50                  55                  60

aca gac cag gga acg gac cca gga ccg ctg tcc acg gac atg acg ttc      240
Thr Asp Gln Gly Thr Asp Pro Gly Pro Leu Ser Thr Asp Met Thr Phe
65                  70                  75                  80

aga gtt gtt ttt gtg ccc acg caa gga gaa cct aga ttc gcg tcc tca      288
Arg Val Val Phe Val Pro Thr Gln Gly Glu Pro Arg Phe Ala Ser Ser
                85                  90                  95

gaa cat gct gtc gct ttc ata gaa aag agt gcc ggc atg gaa gag tct      336
Glu His Ala Val Ala Phe Ile Glu Lys Ser Ala Gly Met Glu Glu Ser
            100                 105                 110

cac caa ctt cct cta gca caa gac atc aag aac cat ctc tgt gaa gac      384
His Gln Leu Pro Leu Ala Gln Asp Ile Lys Asn His Leu Cys Glu Asp
        115                 120                 125

gac tgt cac agc att tac tat cgt att atc gat ggc aac agc gag ggt      432
Asp Cys His Ser Ile Tyr Tyr Arg Ile Ile Asp Gly Asn Ser Glu Gly
    130                 135                 140

cat ttc ggc ctg gat cct gtt cgc aac agg ttg ttc ctg aag aaa gag      480
His Phe Gly Leu Asp Pro Val Arg Asn Arg Leu Phe Leu Lys Lys Glu
145                 150                 155                 160

ctg ata aga gaa caa agt gcc tcc cac act ctg caa gtg gcg gct agt      528
Leu Ile Arg Glu Gln Ser Ala Ser His Thr Leu Gln Val Ala Ala Ser
                165                 170                 175

aac tcg ccc gat ggt ggc att cca ctt cct gct tcc atc ctt act gtc      576
Asn Ser Pro Asp Gly Gly Ile Pro Leu Pro Ala Ser Ile Leu Thr Val
            180                 185                 190

act gtt acc gtg agg gag gca gac cct cgt cca gtg ttt atg agg gaa      624
Thr Val Thr Val Arg Glu Ala Asp Pro Arg Pro Val Phe Met Arg Glu
        195                 200                 205

ttg tac acc gca ggg ata tcc aca gcg gac tcc atc ggc aga gag ctg      672
Leu Tyr Thr Ala Gly Ile Ser Thr Ala Asp Ser Ile Gly Arg Glu Leu
    210                 215                 220

ctc aga tta cat gcg acc cag tct gaa ggc gcg gcc att act tat gct      720
Leu Arg Leu His Ala Thr Gln Ser Glu Gly Ala Ala Ile Thr Tyr Ala
225                 230                 235                 240

ata gac tac gat aca atg gta gtg gac ccc agc ctg gag gca gtg aga      768
Ile Asp Tyr Asp Thr Met Val Val Asp Pro Ser Leu Glu Ala Val Arg
                245                 250                 255
```

```
cag tcg gct ttc gta ctg aac gct caa acc gga gtg ctg acg ctt aat      816
Gln Ser Ala Phe Val Leu Asn Ala Gln Thr Gly Val Leu Thr Leu Asn
            260                 265                 270

atc cag ccc acg gcc acg atg cat gga ctg ttc aaa ttc gaa gtc aca      864
Ile Gln Pro Thr Ala Thr Met His Gly Leu Phe Lys Phe Glu Val Thr
        275                 280                 285

gct act gac acg gcc ggc gct cag gac cgc acc gac gtc acc gtg tac      912
Ala Thr Asp Thr Ala Gly Ala Gln Asp Arg Thr Asp Val Thr Val Tyr
    290                 295                 300

gtg gta tcc tcg cag aac cgc ctc gag cac cac cac cac cac cac tga      960
Val Val Ser Ser Gln Asn Arg Leu Glu His His His His His His
305                 310                 315


<210> SEQ ID NO 2
<211> LENGTH: 319
<212> TYPE: PRT
<213> ORGANISM: Manduca sexta

<400> SEQUENCE: 2

Met His Leu Glu Arg Ile Ser Ala Thr Asp Pro Asp Gly Leu His Ala
1               5                   10                  15

Gly Val Val Thr Phe Gln Val Val Gly Asp Glu Glu Ser Gln Arg Tyr
            20                  25                  30

Phe Gln Val Val Asn Asp Gly Ala Asn Leu Gly Ser Leu Arg Leu Leu
        35                  40                  45

Gln Ala Val Pro Glu Glu Ile Arg Glu Phe Arg Ile Thr Ile Arg Ala
    50                  55                  60

Thr Asp Gln Gly Thr Asp Pro Gly Pro Leu Ser Thr Asp Met Thr Phe
65                  70                  75                  80

Arg Val Val Phe Val Pro Thr Gln Gly Glu Pro Arg Phe Ala Ser Ser
                85                  90                  95

Glu His Ala Val Ala Phe Ile Glu Lys Ser Ala Gly Met Glu Glu Ser
            100                 105                 110

His Gln Leu Pro Leu Ala Gln Asp Ile Lys Asn His Leu Cys Glu Asp
        115                 120                 125

Asp Cys His Ser Ile Tyr Tyr Arg Ile Ile Asp Gly Asn Ser Glu Gly
    130                 135                 140

His Phe Gly Leu Asp Pro Val Arg Asn Arg Leu Phe Leu Lys Lys Glu
145                 150                 155                 160

Leu Ile Arg Glu Gln Ser Ala Ser His Thr Leu Gln Val Ala Ala Ser
                165                 170                 175

Asn Ser Pro Asp Gly Gly Ile Pro Leu Pro Ala Ser Ile Leu Thr Val
            180                 185                 190

Thr Val Thr Val Arg Glu Ala Asp Pro Arg Pro Val Phe Met Arg Glu
        195                 200                 205

Leu Tyr Thr Ala Gly Ile Ser Thr Ala Asp Ser Ile Gly Arg Glu Leu
    210                 215                 220

Leu Arg Leu His Ala Thr Gln Ser Glu Gly Ala Ala Ile Thr Tyr Ala
225                 230                 235                 240

Ile Asp Tyr Asp Thr Met Val Val Asp Pro Ser Leu Glu Ala Val Arg
                245                 250                 255

Gln Ser Ala Phe Val Leu Asn Ala Gln Thr Gly Val Leu Thr Leu Asn
            260                 265                 270

Ile Gln Pro Thr Ala Thr Met His Gly Leu Phe Lys Phe Glu Val Thr
        275                 280                 285
```

```
Ala Thr Asp Thr Ala Gly Ala Gln Asp Arg Thr Asp Val Thr Val Tyr
    290                 295                 300

Val Val Ser Ser Gln Asn Arg Leu Glu His His His His His His
305                 310                 315
```

<210> SEQ ID NO 3
<211> LENGTH: 960
<212> TYPE: DNA
<213> ORGANISM: Artificial sequence
<220> FEATURE:
<223> OTHER INFORMATION: protease stabilized version of SEQ ID NOs: 1 and 2
<220> FEATURE:
<221> NAME/KEY: CDS
<222> LOCATION: (1)..(957)

<400> SEQUENCE: 3

```
atg cac ctg gaa tgt atc tct gca acc gac ccg gat ggc ctg cat gct       48
Met His Leu Glu Cys Ile Ser Ala Thr Asp Pro Asp Gly Leu His Ala
1               5                   10                  15

ggt gta gta act ttc caa gtg gtt ggt gac gaa gaa agc cag gct tat       96
Gly Val Val Thr Phe Gln Val Val Gly Asp Glu Glu Ser Gln Ala Tyr
            20                  25                  30

ttc cag gtt gtt aac gac ggt gca aac ctg ggc tcc ctt tcc ctg ctg      144
Phe Gln Val Val Asn Asp Gly Ala Asn Leu Gly Ser Leu Ser Leu Leu
        35                  40                  45

cag gcc gtg cca gaa gaa atc gca gag ttc agc att acc atc tgc gct      192
Gln Ala Val Pro Glu Glu Ile Ala Glu Phe Ser Ile Thr Ile Cys Ala
    50                  55                  60

acc gac caa ggt acc gac ccg ggc ccg ctg agc acc gac atg acc ttc      240
Thr Asp Gln Gly Thr Asp Pro Gly Pro Leu Ser Thr Asp Met Thr Phe
65                  70                  75                  80

gct gtt gta ttc gtt cct act cag ggt gaa cca gct ttc gct tcc tct      288
Ala Val Val Phe Val Pro Thr Gln Gly Glu Pro Ala Phe Ala Ser Ser
                85                  90                  95

gag cac gca gta gca ttc atc gaa gcc tcc gcg ggt atg gaa gaa tct      336
Glu His Ala Val Ala Phe Ile Glu Ala Ser Ala Gly Met Glu Glu Ser
            100                 105                 110

cat cag ctc cca ctg gct caa gat atc gcg aac cat ctg tgt gaa gac      384
His Gln Leu Pro Leu Ala Gln Asp Ile Ala Asn His Leu Cys Glu Asp
        115                 120                 125

gac tgc cac tct atc tac tac gct atc atc gac ggt aac agc gaa ggt      432
Asp Cys His Ser Ile Tyr Tyr Ala Ile Ile Asp Gly Asn Ser Glu Gly
    130                 135                 140

cac ttc ggt ctg gac ccg gta gct aac gcg ctg ttc ctg tct gct gaa      480
His Phe Gly Leu Asp Pro Val Ala Asn Ala Leu Phe Leu Ser Ala Glu
145                 150                 155                 160

ctg atc gcg gaa cag agc gct tct cac act tta caa gtt gct gcg tcc      528
Leu Ile Ala Glu Gln Ser Ala Ser His Thr Leu Gln Val Ala Ala Ser
                165                 170                 175

aac agc ccg gac ggt ggc atc cct ctg cct gca tct atc ctt acc gtt      576
Asn Ser Pro Asp Gly Gly Ile Pro Leu Pro Ala Ser Ile Leu Thr Val
            180                 185                 190

acc gta acc gtc gct gaa gca gat cca gca ccg gta ttc atg gct gag      624
Thr Val Thr Val Ala Glu Ala Asp Pro Ala Pro Val Phe Met Ala Glu
        195                 200                 205

ctg tac acg gct ggc atc agc act gcc gac tcc att ggc tgc gaa ctt      672
Leu Tyr Thr Ala Gly Ile Ser Thr Ala Asp Ser Ile Gly Cys Glu Leu
    210                 215                 220

ctg gct ctg cat gcg act cag tca gaa ggc gcg gcc atc acc tat gct      720
Leu Ala Leu His Ala Thr Gln Ser Glu Gly Ala Ala Ile Thr Tyr Ala
225                 230                 235                 240
```

-continued

```
atc gac tat gat acc atg gta gtt gat ccg tct ctg gaa gca gtt tgc      768
Ile Asp Tyr Asp Thr Met Val Val Asp Pro Ser Leu Glu Ala Val Cys
                245                 250                 255

cag tct gct ttc gtt ctg aac gca cag act ggt gtt ctg act ctg aac      816
Gln Ser Ala Phe Val Leu Asn Ala Gln Thr Gly Val Leu Thr Leu Asn
            260                 265                 270

atc cag ccg act gca acg atg cat ggt ctg ttc aac ttc gaa gtt act      864
Ile Gln Pro Thr Ala Thr Met His Gly Leu Phe Asn Phe Glu Val Thr
        275                 280                 285

gcg acc gac act gcg ggc gct cag gac cgt act gac gtt acc gtc tac      912
Ala Thr Asp Thr Ala Gly Ala Gln Asp Arg Thr Asp Val Thr Val Tyr
    290                 295                 300

gta gtg tct tct cag aac cgt ctg gaa cac cac cac cac cac cac taa      960
Val Val Ser Ser Gln Asn Arg Leu Glu His His His His His His
305                 310                 315


<210> SEQ ID NO 4
<211> LENGTH: 319
<212> TYPE: PRT
<213> ORGANISM: Artificial sequence
<220> FEATURE:
<223> OTHER INFORMATION: protease stabilized version of SEQ ID NOs: 1
      and 2

<400> SEQUENCE: 4

Met His Leu Glu Cys Ile Ser Ala Thr Asp Pro Asp Gly Leu His Ala
1               5                   10                  15

Gly Val Val Thr Phe Gln Val Val Gly Asp Glu Glu Ser Gln Ala Tyr
            20                  25                  30

Phe Gln Val Val Asn Asp Gly Ala Asn Leu Gly Ser Leu Ser Leu Leu
        35                  40                  45

Gln Ala Val Pro Glu Glu Ile Ala Glu Phe Ser Ile Thr Ile Cys Ala
    50                  55                  60

Thr Asp Gln Gly Thr Asp Pro Gly Pro Leu Ser Thr Asp Met Thr Phe
65                  70                  75                  80

Ala Val Val Phe Val Pro Thr Gln Gly Glu Pro Ala Phe Ala Ser Ser
                85                  90                  95

Glu His Ala Val Ala Phe Ile Glu Ala Ser Ala Gly Met Glu Glu Ser
            100                 105                 110

His Gln Leu Pro Leu Ala Gln Asp Ile Ala Asn His Leu Cys Glu Asp
        115                 120                 125

Asp Cys His Ser Ile Tyr Tyr Ala Ile Ile Asp Gly Asn Ser Glu Gly
    130                 135                 140

His Phe Gly Leu Asp Pro Val Ala Asn Ala Leu Phe Leu Ser Ala Glu
145                 150                 155                 160

Leu Ile Ala Glu Gln Ser Ala Ser His Thr Leu Gln Val Ala Ala Ser
                165                 170                 175

Asn Ser Pro Asp Gly Gly Ile Pro Leu Pro Ala Ser Ile Leu Thr Val
            180                 185                 190

Thr Val Thr Val Ala Glu Ala Asp Pro Ala Pro Val Phe Met Ala Glu
        195                 200                 205

Leu Tyr Thr Ala Gly Ile Ser Thr Ala Asp Ser Ile Gly Cys Glu Leu
    210                 215                 220

Leu Ala Leu His Ala Thr Gln Ser Glu Gly Ala Ala Ile Thr Tyr Ala
225                 230                 235                 240

Ile Asp Tyr Asp Thr Met Val Val Asp Pro Ser Leu Glu Ala Val Cys
                245                 250                 255
```

-continued

```
Gln Ser Ala Phe Val Leu Asn Ala Gln Thr Gly Val Leu Thr Leu Asn
            260                 265                 270

Ile Gln Pro Thr Ala Thr Met His Gly Leu Phe Asn Phe Glu Val Thr
        275                 280                 285

Ala Thr Asp Thr Ala Gly Ala Gln Asp Arg Thr Asp Val Thr Val Tyr
    290                 295                 300

Val Val Ser Ser Gln Asn Arg Leu Glu His His His His His His
305                 310                 315


<210> SEQ ID NO 5
<211> LENGTH: 1160
<212> TYPE: DNA
<213> ORGANISM: Artificial sequence
<220> FEATURE:
<223> OTHER INFORMATION: version of SEQ ID NO: 6 with cloning sites

<400> SEQUENCE: 5

gaattcaagg agatatacat atggctgttc ttatgactaa agacctgcag tgctctgaaa      60

acctgaacaa ggatggtgaa gtaggtgagg gcatcattgg tgaagacatt gatgatggtg     120

acaacgctaa aattgacttc tctgttttgt ctattgtaga taaggaaact aagaacgaca     180

tccaggaatc ctttaacatc tccaaaattg attctgatta tgtgctcaac gacactctga     240

agaaagtaca cctgattgct tttgaagatc tgaaaggtaa atatggaacc tatgaagtaa     300

ccctccacat gcatgatgaa ggtgacccaa tgcagactac tgacccagat ccaaccctga     360

ccctgaccat tgagaaatgg aactaccaga cccctagcat tattttccca gagaacgacc     420

agacctacat tgtgctgagc gaccagcagc ctggtcagcc actggcactg tttaacaaca     480

ctggtacatc caacactctg ccagacttct cagctactga tggtgagact aaagactata     540

gcaaatggga tgtaaagttc agctacaccc agaccaacta tgaagatgac aagatctttg     600

ttattgatca catccagcca tgcgtttccc agcttcaggt tagcaaacac ttcaactctg     660

acctggttcg ctccaagaaa tacaaactga ctatcactgc ttctgtgaag gatggtgctg     720

aacaggaagg tgaggctggc tactctactt ctgcaaacat ctctattgtt ttcctgaaca     780

acgatgctca gccaatcttt cagaactctg actggtctgt ttcctttgtt gagttcaaca     840

ccactcagcc agcaaaacca ctggaagaac aggcagaata tgaaaacacc aagggtggcc     900

tgccgatcta ttaccatttc tactctgaaa accagaccct gtccaaatac tttgaggttg     960

atgagacttc tggtgacctg tctgttattg gtaacctgac ttatgactat gaccaggaca    1020

tcagctttca cattgttgct tccaacgatt ctcaggtacg catgctggac ccacgctctt    1080

ctctgaacgt aactgtaaac ttcctgccac gtaaccgtcg tgccccacag tggcaccacc    1140

accaccacca ctaaaagctt                                                1160


<210> SEQ ID NO 6
<211> LENGTH: 1134
<212> TYPE: DNA
<213> ORGANISM: Diabrotica virgifera
<220> FEATURE:
<221> NAME/KEY: CDS
<222> LOCATION: (1)..(1131)

<400> SEQUENCE: 6

atg gct gtt ctt atg act aaa gac ctg cag tgc tct gaa aac ctg aac       48
Met Ala Val Leu Met Thr Lys Asp Leu Gln Cys Ser Glu Asn Leu Asn
1               5                   10                  15

aag gat ggt gaa gta ggt gag ggc atc att ggt gaa gac att gat gat       96
Lys Asp Gly Glu Val Gly Glu Gly Ile Ile Gly Glu Asp Ile Asp Asp
            20                  25                  30
```

-continued

```
ggt gac aac gct aaa att gac ttc tct gtt ttg tct att gta gat aag      144
Gly Asp Asn Ala Lys Ile Asp Phe Ser Val Leu Ser Ile Val Asp Lys
        35                  40                  45

gaa act aag aac gac atc cag gaa tcc ttt aac atc tcc aaa att gat      192
Glu Thr Lys Asn Asp Ile Gln Glu Ser Phe Asn Ile Ser Lys Ile Asp
    50                  55                  60

tct gat tat gtg ctc aac gac act ctg aag aaa gta cac ctg att gct      240
Ser Asp Tyr Val Leu Asn Asp Thr Leu Lys Lys Val His Leu Ile Ala
65                  70                  75                  80

ttt gaa gat ctg aaa ggt aaa tat gga acc tat gaa gta acc ctc cac      288
Phe Glu Asp Leu Lys Gly Lys Tyr Gly Thr Tyr Glu Val Thr Leu His
                85                  90                  95

atg cat gat gaa ggt gac cca atg cag act act gac cca gat cca acc      336
Met His Asp Glu Gly Asp Pro Met Gln Thr Thr Asp Pro Asp Pro Thr
            100                 105                 110

ctg acc ctg acc att gag aaa tgg aac tac cag acc cct agc att att      384
Leu Thr Leu Thr Ile Glu Lys Trp Asn Tyr Gln Thr Pro Ser Ile Ile
        115                 120                 125

ttc cca gaa aac gac cag acc tac att gtg ctg agc gac cag cag cct      432
Phe Pro Glu Asn Asp Gln Thr Tyr Ile Val Leu Ser Asp Gln Gln Pro
    130                 135                 140

ggt cag cca ctg gca ctg ttt aac aac act ggt aca tcc aac act ctg      480
Gly Gln Pro Leu Ala Leu Phe Asn Asn Thr Gly Thr Ser Asn Thr Leu
145                 150                 155                 160

cca gac ttc tca gct act gat ggt gag act aaa gac tat agc aaa tgg      528
Pro Asp Phe Ser Ala Thr Asp Gly Glu Thr Lys Asp Tyr Ser Lys Trp
                165                 170                 175

gat gta aag ttc agc tac acc cag acc aac tat gaa gat gac aag atc      576
Asp Val Lys Phe Ser Tyr Thr Gln Thr Asn Tyr Glu Asp Asp Lys Ile
            180                 185                 190

ttt gtt att gat cac atc cag cca tgc gtt tcc cag ctt cag gtt agc      624
Phe Val Ile Asp His Ile Gln Pro Cys Val Ser Gln Leu Gln Val Ser
        195                 200                 205

aaa cac ttc aac tct gac ctg gtt cgc tcc aag aaa tac aaa ctg act      672
Lys His Phe Asn Ser Asp Leu Val Arg Ser Lys Lys Tyr Lys Leu Thr
    210                 215                 220

atc act gct tct gtg aag gat ggt gct gaa cag gaa ggt gag gct ggc      720
Ile Thr Ala Ser Val Lys Asp Gly Ala Glu Gln Glu Gly Glu Ala Gly
225                 230                 235                 240

tac tct act tct gca aac atc tct att gtt ttc ctg aac aac gat gct      768
Tyr Ser Thr Ser Ala Asn Ile Ser Ile Val Phe Leu Asn Asn Asp Ala
                245                 250                 255

cag cca atc ttt cag aac tct gac tgg tct gtt tcc ttt gtt gag ttc      816
Gln Pro Ile Phe Gln Asn Ser Asp Trp Ser Val Ser Phe Val Glu Phe
            260                 265                 270

aac acc act cag cca gca aaa cca ctg gaa gaa cag gca gaa tat gaa      864
Asn Thr Thr Gln Pro Ala Lys Pro Leu Glu Glu Gln Ala Glu Tyr Glu
        275                 280                 285

aac acc aag ggt ggc ctg ccg atc tat tac cat ttc tac tct gaa aac      912
Asn Thr Lys Gly Gly Leu Pro Ile Tyr Tyr His Phe Tyr Ser Glu Asn
    290                 295                 300

cag acc ctg tcc aaa tac ttt gag gtt gat gag act tct ggt gac ctg      960
Gln Thr Leu Ser Lys Tyr Phe Glu Val Asp Glu Thr Ser Gly Asp Leu
305                 310                 315                 320

tct gtt att ggt aac ctg act tat gac tat gac cag gac atc agc ttt     1008
Ser Val Ile Gly Asn Leu Thr Tyr Asp Tyr Asp Gln Asp Ile Ser Phe
                325                 330                 335

cac att gtt gct tcc aac gat tct cag gta cgc atg ctg gac cca cgc     1056
His Ile Val Ala Ser Asn Asp Ser Gln Val Arg Met Leu Asp Pro Arg
            340                 345                 350
```

-continued

```
tct tct ctg aac gta act gta aac ttc ctg cca cgt aac cgt cgt gcc      1104
Ser Ser Leu Asn Val Thr Val Asn Phe Leu Pro Arg Asn Arg Arg Ala
        355                 360                 365

cca cag tgg cac cac cac cac cac cac taa                              1134
Pro Gln Trp His His His His His His
    370                 375


<210> SEQ ID NO 7
<211> LENGTH: 377
<212> TYPE: PRT
<213> ORGANISM: Diabrotica virgifera

<400> SEQUENCE: 7

Met Ala Val Leu Met Thr Lys Asp Leu Gln Cys Ser Glu Asn Leu Asn
1               5                   10                  15

Lys Asp Gly Glu Val Gly Glu Gly Ile Ile Gly Glu Asp Ile Asp Asp
            20                  25                  30

Gly Asp Asn Ala Lys Ile Asp Phe Ser Val Leu Ser Ile Val Asp Lys
        35                  40                  45

Glu Thr Lys Asn Asp Ile Gln Glu Ser Phe Asn Ile Ser Lys Ile Asp
    50                  55                  60

Ser Asp Tyr Val Leu Asn Asp Thr Leu Lys Lys Val His Leu Ile Ala
65                  70                  75                  80

Phe Glu Asp Leu Lys Gly Lys Tyr Gly Thr Tyr Glu Val Thr Leu His
                85                  90                  95

Met His Asp Glu Gly Asp Pro Met Gln Thr Thr Asp Pro Asp Pro Thr
            100                 105                 110

Leu Thr Leu Thr Ile Glu Lys Trp Asn Tyr Gln Thr Pro Ser Ile Ile
        115                 120                 125

Phe Pro Glu Asn Asp Gln Thr Tyr Ile Val Leu Ser Asp Gln Gln Pro
    130                 135                 140

Gly Gln Pro Leu Ala Leu Phe Asn Asn Thr Gly Thr Ser Asn Thr Leu
145                 150                 155                 160

Pro Asp Phe Ser Ala Thr Asp Gly Glu Thr Lys Asp Tyr Ser Lys Trp
                165                 170                 175

Asp Val Lys Phe Ser Tyr Thr Gln Thr Asn Tyr Glu Asp Asp Lys Ile
            180                 185                 190

Phe Val Ile Asp His Ile Gln Pro Cys Val Ser Gln Leu Gln Val Ser
        195                 200                 205

Lys His Phe Asn Ser Asp Leu Val Arg Ser Lys Lys Tyr Lys Leu Thr
    210                 215                 220

Ile Thr Ala Ser Val Lys Asp Gly Ala Glu Gln Glu Gly Glu Ala Gly
225                 230                 235                 240

Tyr Ser Thr Ser Ala Asn Ile Ser Ile Val Phe Leu Asn Asn Asp Ala
                245                 250                 255

Gln Pro Ile Phe Gln Asn Ser Asp Trp Ser Val Ser Phe Val Glu Phe
            260                 265                 270

Asn Thr Thr Gln Pro Ala Lys Pro Leu Glu Glu Gln Ala Glu Tyr Glu
        275                 280                 285

Asn Thr Lys Gly Gly Leu Pro Ile Tyr Tyr His Phe Tyr Ser Glu Asn
    290                 295                 300

Gln Thr Leu Ser Lys Tyr Phe Glu Val Asp Glu Thr Ser Gly Asp Leu
305                 310                 315                 320

Ser Val Ile Gly Asn Leu Thr Tyr Asp Tyr Asp Gln Asp Ile Ser Phe
                325                 330                 335
```

-continued

```
His Ile Val Ala Ser Asn Asp Ser Gln Val Arg Met Leu Asp Pro Arg
            340                 345                 350

Ser Ser Leu Asn Val Thr Val Asn Phe Leu Pro Arg Asn Arg Arg Ala
        355                 360                 365

Pro Gln Trp His His His His His His
    370                 375


<210> SEQ ID NO 8
<211> LENGTH: 639
<212> TYPE: DNA
<213> ORGANISM: Artificial sequence
<220> FEATURE:
<223> OTHER INFORMATION: version of SEQ ID NO: 9 with added cloning
      sites

<400> SEQUENCE: 8

gaattcatga aacagtggta tcagcgtcgt gttgccatca ccgcaggtaa agacaccacc      60

tctaaagaca aactgcagta caacatcgac aacatcaccc cgtccaacct ggacctggac     120

atcaaatccg cgttcactat gaacactcag agcggtgata tcaccatcaa ctttgaggtt     180

aaagactcta tggaaggcta cttcaccctg gacctgtccg tacaggatga agaaccggaa     240

aaccacaaag ctgacgcaac cctgaaaatc tacattgtaa cctctaagaa cactgtagtt     300

ttccgcttcg aaaacgacca ggaaactgtt agcgacaaag cgggggacat caaatctgta     360

ctcgacgaag aattccagta cgaaaccaaa gttgaagccc cgacaggtaa caccactgac     420

ggtacgccgc tgacccgtag cccggttttc ttcctgaacc tcaacaccaa tgaaccggtt     480

gacgctaccg agatcctgaa gaaagttact aacgtagatg ttttccagcg tctgaagaac     540

aacttctcta aagttggcct ggttctgctg tccttcgact ctagctctga gactaacgaa     600

aacctggagg cacatcatca tcatcatcat taaaagctt                            639


<210> SEQ ID NO 9
<211> LENGTH: 627
<212> TYPE: DNA
<213> ORGANISM: Tenebrio molitor
<220> FEATURE:
<221> NAME/KEY: CDS
<222> LOCATION: (1)..(624)

<400> SEQUENCE: 9

atg aaa cag tgg tat cag cgt cgt gtt gcc atc acc gca ggt aaa gac       48
Met Lys Gln Trp Tyr Gln Arg Arg Val Ala Ile Thr Ala Gly Lys Asp
1               5                   10                  15

acc acc tct aaa gac aaa ctg cag tac aac atc gac aac atc acc ccg       96
Thr Thr Ser Lys Asp Lys Leu Gln Tyr Asn Ile Asp Asn Ile Thr Pro
            20                  25                  30

tcc aac ctg gac ctg gac atc aaa tcc gcg ttc act atg aac act cag      144
Ser Asn Leu Asp Leu Asp Ile Lys Ser Ala Phe Thr Met Asn Thr Gln
        35                  40                  45

agc ggt gat atc acc atc aac ttt gag gtt aaa gac tct atg gaa ggc      192
Ser Gly Asp Ile Thr Ile Asn Phe Glu Val Lys Asp Ser Met Glu Gly
    50                  55                  60

tac ttc acc ctg gac ctg tcc gta cag gat gaa gaa ccg gaa aac cac      240
Tyr Phe Thr Leu Asp Leu Ser Val Gln Asp Glu Glu Pro Glu Asn His
65                  70                  75                  80

aaa gct gac gca acc ctg aaa atc tac att gta acc tct aag aac act      288
Lys Ala Asp Ala Thr Leu Lys Ile Tyr Ile Val Thr Ser Lys Asn Thr
                85                  90                  95

gta gtt ttc cgc ttc gaa aac gac cag gaa act gtt agc gac aaa gcg      336
Val Val Phe Arg Phe Glu Asn Asp Gln Glu Thr Val Ser Asp Lys Ala
            100                 105                 110
```

-continued

```
ggg gac atc aaa tct gta ctc gac gaa gaa ttc cag tac gaa acc aaa      384
Gly Asp Ile Lys Ser Val Leu Asp Glu Glu Phe Gln Tyr Glu Thr Lys
        115                 120                 125

gtt gaa gcc ccg aca ggt aac acc act gac ggt acg ccg ctg acc cgt      432
Val Glu Ala Pro Thr Gly Asn Thr Thr Asp Gly Thr Pro Leu Thr Arg
    130                 135                 140

agc ccg gtt ttc ttc ctg aac ctc aac acc aat gaa ccg gtt gac gct      480
Ser Pro Val Phe Phe Leu Asn Leu Asn Thr Asn Glu Pro Val Asp Ala
145                 150                 155                 160

acc gag atc ctg aag aaa gtt act aac gta gat gtt ttc cag cgt ctg      528
Thr Glu Ile Leu Lys Lys Val Thr Asn Val Asp Val Phe Gln Arg Leu
                165                 170                 175

aag aac aac ttc tct aaa gtt ggc ctg gtt ctg ctg tcc ttc gac tct      576
Lys Asn Asn Phe Ser Lys Val Gly Leu Val Leu Leu Ser Phe Asp Ser
            180                 185                 190

agc tct gag act aac gaa aac ctg gag gca cat cat cat cat cat cat      624
Ser Ser Glu Thr Asn Glu Asn Leu Glu Ala His His His His His His
        195                 200                 205

taa                                                                  627
```

<210> SEQ ID NO 10
<211> LENGTH: 208
<212> TYPE: PRT
<213> ORGANISM: Tenebrio molitor

<400> SEQUENCE: 10

```
Met Lys Gln Trp Tyr Gln Arg Arg Val Ala Ile Thr Ala Gly Lys Asp
1               5                   10                  15

Thr Thr Ser Lys Asp Lys Leu Gln Tyr Asn Ile Asp Asn Ile Thr Pro
            20                  25                  30

Ser Asn Leu Asp Leu Asp Ile Lys Ser Ala Phe Thr Met Asn Thr Gln
        35                  40                  45

Ser Gly Asp Ile Thr Ile Asn Phe Glu Val Lys Asp Ser Met Glu Gly
    50                  55                  60

Tyr Phe Thr Leu Asp Leu Ser Val Gln Asp Glu Glu Pro Glu Asn His
65                  70                  75                  80

Lys Ala Asp Ala Thr Leu Lys Ile Tyr Ile Val Thr Ser Lys Asn Thr
                85                  90                  95

Val Val Phe Arg Phe Glu Asn Asp Gln Glu Thr Val Ser Asp Lys Ala
            100                 105                 110

Gly Asp Ile Lys Ser Val Leu Asp Glu Glu Phe Gln Tyr Glu Thr Lys
        115                 120                 125

Val Glu Ala Pro Thr Gly Asn Thr Thr Asp Gly Thr Pro Leu Thr Arg
    130                 135                 140

Ser Pro Val Phe Phe Leu Asn Leu Asn Thr Asn Glu Pro Val Asp Ala
145                 150                 155                 160

Thr Glu Ile Leu Lys Lys Val Thr Asn Val Asp Val Phe Gln Arg Leu
                165                 170                 175

Lys Asn Asn Phe Ser Lys Val Gly Leu Val Leu Leu Ser Phe Asp Ser
            180                 185                 190

Ser Ser Glu Thr Asn Glu Asn Leu Glu Ala His His His His His His
        195                 200                 205
```

<210> SEQ ID NO 11
<211> LENGTH: 1134
<212> TYPE: DNA
<213> ORGANISM: Artificial sequence -continued

```
<220> FEATURE:
<223> OTHER INFORMATION: protease-stabilized version of SEQ ID NOs: 6
      and 7
<220> FEATURE:
<221> NAME/KEY: CDS
<222> LOCATION: (1)..(1131)

<400> SEQUENCE: 11

atg gct gta ctg atg acc tgt gac ctg cag tgt tct gaa aac ctg aac       48
Met Ala Val Leu Met Thr Cys Asp Leu Gln Cys Ser Glu Asn Leu Asn
1               5                   10                  15

tct gat ggt gaa gtt ggt gag ggt atc att ggt gaa gac att gat gat       96
Ser Asp Gly Glu Val Gly Glu Gly Ile Ile Gly Glu Asp Ile Asp Asp
            20                  25                  30

ggt gac aat gct tgc att gac ttc tct gtt ctg tct att gtt gac agt      144
Gly Asp Asn Ala Cys Ile Asp Phe Ser Val Leu Ser Ile Val Asp Ser
        35                  40                  45

gaa act tct aat gac atc cag gaa tcc ttc aac atc tct tgc att gac      192
Glu Thr Ser Asn Asp Ile Gln Glu Ser Phe Asn Ile Ser Cys Ile Asp
    50                  55                  60

tct gac tat gtc ctg aat gat acc ctg tct tct gtt cac ctc att gct      240
Ser Asp Tyr Val Leu Asn Asp Thr Leu Ser Ser Val His Leu Ile Ala
65                  70                  75                  80

ttt gag gat ctg tct ggt tcc tat ggc acc tat gaa gta acc ctg cac      288
Phe Glu Asp Leu Ser Gly Ser Tyr Gly Thr Tyr Glu Val Thr Leu His
                85                  90                  95

atg cat gat gaa ggt gac cca atg cag act act gac cca gac cct acc      336
Met His Asp Glu Gly Asp Pro Met Gln Thr Thr Asp Pro Asp Pro Thr
            100                 105                 110

ctg acc ctg act att gaa tct tgg aat tac cag act cca tct atc atc      384
Leu Thr Leu Thr Ile Glu Ser Trp Asn Tyr Gln Thr Pro Ser Ile Ile
        115                 120                 125

ttc cca gag aat gac cag acc tac att gta ctg tct gac cag caa cca      432
Phe Pro Glu Asn Asp Gln Thr Tyr Ile Val Leu Ser Asp Gln Gln Pro
    130                 135                 140

ggc cag cct ctg gct ctg ttt aac aac act ggc acc tct aac act ctc      480
Gly Gln Pro Leu Ala Leu Phe Asn Asn Thr Gly Thr Ser Asn Thr Leu
145                 150                 155                 160

cca gac ttc agt gct act gat ggt gaa act tct gac tat tcc tgc tgg      528
Pro Asp Phe Ser Ala Thr Asp Gly Glu Thr Ser Asp Tyr Ser Cys Trp
                165                 170                 175

gat gtt tct ttc agc tac acc cag act aac tat gaa gat gac tca atc      576
Asp Val Ser Phe Ser Tyr Thr Gln Thr Asn Tyr Glu Asp Asp Ser Ile
            180                 185                 190

ttt gtt att gac cac atc cag cca tgt gtg tcc cag ctg cag gtt tct      624
Phe Val Ile Asp His Ile Gln Pro Cys Val Ser Gln Leu Gln Val Ser
        195                 200                 205

gct cac ttc aac tct gat ctg gta gct tct tgc tct tat gct ctg acc      672
Ala His Phe Asn Ser Asp Leu Val Ala Ser Cys Ser Tyr Ala Leu Thr
    210                 215                 220

atc act gct tct gtt gct gat ggt gca gaa caa gaa ggt gaa gct ggt      720
Ile Thr Ala Ser Val Ala Asp Gly Ala Glu Gln Glu Gly Glu Ala Gly
225                 230                 235                 240

tat tcc act tct gct aac att tct att gta ttc ctg aac aac gat gca      768
Tyr Ser Thr Ser Ala Asn Ile Ser Ile Val Phe Leu Asn Asn Asp Ala
                245                 250                 255

cag cca atc ttc cag aac tct gac tgg agt gtt agc ttt gtt gaa ttt      816
Gln Pro Ile Phe Gln Asn Ser Asp Trp Ser Val Ser Phe Val Glu Phe
            260                 265                 270

aac acc act cag cca gca tct cct ctt gaa gaa cag gct gaa tat gag      864
Asn Thr Thr Gln Pro Ala Ser Pro Leu Glu Glu Gln Ala Glu Tyr Glu
        275                 280                 285
```

aac acc tct ggt ggt ctg cca atc tac tac cac ttc tat tct gaa aac 912
Asn Thr Ser Gly Gly Leu Pro Ile Tyr Tyr His Phe Tyr Ser Glu Asn
290 295 300 cag acc ctg tcc tgt tac ttt gaa gta gat gag acc agt ggt gat ctg 960
Gln Thr Leu Ser Cys Tyr Phe Glu Val Asp Glu Thr Ser Gly Asp Leu
305 310 315 320 agt gtg att ggt aac ctg act tat gac tat gat caa gac atc tct ttc 1008
Ser Val Ile Gly Asn Leu Thr Tyr Asp Tyr Asp Gln Asp Ile Ser Phe
325 330 335 cac att gtt gca tct aat gac tcc cag gta tcc atg ctg gac cca tgc 1056
His Ile Val Ala Ser Asn Asp Ser Gln Val Ser Met Leu Asp Pro Cys
340 345 350 tct tct ctg aac gtt act gtt aac ttc ctg cct gct aac aga cgt gct 1104
Ser Ser Leu Asn Val Thr Val Asn Phe Leu Pro Ala Asn Arg Arg Ala
355 360 365 cca cag tgg cac cac cac cac cat cac taa 1134
Pro Gln Trp His His His His His His
370 375

<210> SEQ ID NO 12
<211> LENGTH: 377
<212> TYPE: PRT
<213> ORGANISM: Artificial sequence
<220> FEATURE:
<223> OTHER INFORMATION: protease-stabilized version of SEQ ID NOs: 6 and 7

<400> SEQUENCE: 12

Met Ala Val Leu Met Thr Cys Asp Leu Gln Cys Ser Glu Asn Leu Asn
1 5 10 15

Ser Asp Gly Glu Val Gly Glu Gly Ile Ile Gly Glu Asp Ile Asp Asp
20 25 30

Gly Asp Asn Ala Cys Ile Asp Phe Ser Val Leu Ser Ile Val Asp Ser
35 40 45

Glu Thr Ser Asn Asp Ile Gln Glu Ser Phe Asn Ile Ser Cys Ile Asp
50 55 60

Ser Asp Tyr Val Leu Asn Asp Thr Leu Ser Ser Val His Leu Ile Ala
65 70 75 80

Phe Glu Asp Leu Ser Gly Ser Tyr Gly Thr Tyr Glu Val Thr Leu His
85 90 95

Met His Asp Glu Gly Asp Pro Met Gln Thr Thr Asp Pro Asp Pro Thr
100 105 110

Leu Thr Leu Thr Ile Glu Ser Trp Asn Tyr Gln Thr Pro Ser Ile Ile
115 120 125

Phe Pro Glu Asn Asp Gln Thr Tyr Ile Val Leu Ser Asp Gln Gln Pro
130 135 140

Gly Gln Pro Leu Ala Leu Phe Asn Asn Thr Gly Thr Ser Asn Thr Leu
145 150 155 160

Pro Asp Phe Ser Ala Thr Asp Gly Glu Thr Ser Asp Tyr Ser Cys Trp
165 170 175

Asp Val Ser Phe Ser Tyr Thr Gln Thr Asn Tyr Glu Asp Asp Ser Ile
180 185 190

Phe Val Ile Asp His Ile Gln Pro Cys Val Ser Gln Leu Gln Val Ser
195 200 205

Ala His Phe Asn Ser Asp Leu Val Ala Ser Cys Ser Tyr Ala Leu Thr
210 215 220

Ile Thr Ala Ser Val Ala Asp Gly Ala Glu Gln Glu Gly Glu Ala Gly
225 230 235 240

-continued

```
Tyr Ser Thr Ser Ala Asn Ile Ser Ile Val Phe Leu Asn Asn Asp Ala
                245                 250                 255

Gln Pro Ile Phe Gln Asn Ser Asp Trp Ser Val Ser Phe Val Glu Phe
            260                 265                 270

Asn Thr Thr Gln Pro Ala Ser Pro Leu Glu Glu Gln Ala Glu Tyr Glu
        275                 280                 285

Asn Thr Ser Gly Gly Leu Pro Ile Tyr Tyr His Phe Tyr Ser Glu Asn
    290                 295                 300

Gln Thr Leu Ser Cys Tyr Phe Glu Val Asp Glu Thr Ser Gly Asp Leu
305                 310                 315                 320

Ser Val Ile Gly Asn Leu Thr Tyr Asp Tyr Asp Gln Asp Ile Ser Phe
                325                 330                 335

His Ile Val Ala Ser Asn Asp Ser Gln Val Ser Met Leu Asp Pro Cys
            340                 345                 350

Ser Ser Leu Asn Val Thr Val Asn Phe Leu Pro Ala Asn Arg Arg Ala
        355                 360                 365

Pro Gln Trp His His His His His His
    370                 375
```